US009347047B2

(12) United States Patent
Hoshino et al.

(10) Patent No.: US 9,347,047 B2
(45) Date of Patent: May 24, 2016

(54) MODIFIED LEUCINE DEHYDROGENASE

(71) Applicant: AJINOMOTO CO., INC., Tokyo (JP)

(72) Inventors: Wataru Hoshino, Kanagawa (JP); Yuya Kodama, Kanagawa (JP); Toshimi Mizukoshi, Kanagawa (JP); Uno Tagami, Kanagawa (JP)

(73) Assignee: AJINOMOTO CO., INC., Tokyo (JP)

( * ) Notice: Subject to any disclaimer, the term of this patent is extended or adjusted under 35 U.S.C. 154(b) by 0 days.

(21) Appl. No.: 14/491,501

(22) Filed: Sep. 19, 2014

(65) Prior Publication Data

US 2015/0010936 A1 Jan. 8, 2015

Related U.S. Application Data

(63) Continuation of application No. PCT/JP2013/059124, filed on Mar. 27, 2013.

(51) Int. Cl.
*C12N 9/06* (2006.01)
*C12P 41/00* (2006.01)
*C12Q 1/32* (2006.01)
*G01N 33/68* (2006.01)

(52) U.S. Cl.
CPC ................ *C12N 9/0016* (2013.01); *C12Q 1/32* (2013.01); *G01N 33/6812* (2013.01); *C07K 2319/02* (2013.01); *C12Y 104/01009* (2013.01)

(58) Field of Classification Search
CPC .............................. C12N 9/0012; C12P 41/00
USPC ................................ 435/183, 252.3, 320.1, 6
See application file for complete search history.

(56) References Cited

U.S. PATENT DOCUMENTS

| | | | |
|---|---|---|---|
| 2004/0115691 | A1 | 6/2004 | Rozzell et al. |
| 2007/0031913 | A1 | 2/2007 | Kimura |
| 2013/0071863 | A1 | 3/2013 | Kubota et al. |
| 2014/0120233 | A1 | 5/2014 | Kato et al. |

FOREIGN PATENT DOCUMENTS

| | | |
|---|---|---|
| JP | 08-056660 | 3/1996 |
| JP | 2007-289096 | 11/2007 |
| WO | WO2005/075970 | 8/2005 |

OTHER PUBLICATIONS

Okazaki et al., PIR80 database, accession No. 139939, 1996.*
Database UniPrit [online], Accession No. G2RIKO, Complete Genome Sequence of the Industrial Strain Bacillus megaterium WSH-002, Nov. 16, 2011 uploaded [retrieved on May 21, 2013], & J. Bacteriol. 193;6389-6390.
Oikawa, T., et al., "Fragmentary Form of Thermostable Leucine Dehydrogenase of Bacillus stearothermophilus: Its Construction and Reconstitution of Active Fragmentary Enzyme," Biochem. Biophys. Res. Comm. 2001;280:1177-1182.
International Search Report for PCT Patent App. No. PCT/JP2013/059124 (May 28, 2013).

* cited by examiner

*Primary Examiner* — Maryam Monshipouri
(74) *Attorney, Agent, or Firm* — Shelly Guest Cermak; Cermak Nakajima & McGowan LLP

(57) ABSTRACT

The present invention provides a means and method useful for measurement of a total branched-chain amino acid concentration. Specifically, the present invention provides a modified enzyme in which at least one amino acid residue is mutated so as to improve a property of a leucine dehydrogenase which is associated with the measurement of the total branched-chain amino acids, such as, for example, substrate specificities of leucine dehydrogenase for total branched-chain amino acids, activity of leucine dehydrogenase for any branched-chain amino acids, and thermal stability of leucine dehydrogenase; and a method of analyzing the total branched-chain amino acids, comprising measuring the total branched-chain amino acids contained in a test sample using the modified enzyme.

6 Claims, 4 Drawing Sheets

SEQUENCE LISTING

```
<160> NUMBER OF SEQ ID NOS: 10

<210> SEQ ID NO 1
<211> LENGTH: 1104
<212> TYPE: DNA
<213> ORGANISM: Geobacillus stearothermophilus

<400> SEQUENCE: 1

atggaattgt tcaaatatat ggaaacttac gattatgagc aagtgctgtt ttgccaagat     60

aaagaatcgg gtttgaaagc gatcattgcc attcatgaca caacgctcgg cccggcgctc    120

ggcgggacgc gcatgtggat gtacaattcg gaagaagaag cgcttgaaga cgccttgcgc    180

ctcgcccgcg gcatgacgta caaaaacgcg gccgccggcc tcaacttggg cgggggcaaa    240

acggtcatca tcggcgaccc gcgcaaagat aaaaacgaag cgatgttccg ggcgttcggc    300

cgcttcattc aagggctgaa cggccgctac atcacggcgg aagacgtcgg cacgaccgtc    360

gccgatatgg atatcatcta tcaagaaacc gactatgtca ccggcatttc gcccgaattc    420

ggctcatccg gcaacccatc gccggcgacc gcctacggcg tataccgcgg catgaaggcg    480

gcggcaaaag aggcgttcgg cagcgattcg ctcgaaggaa aagtcgtcgc cgtccaagga    540

gtcggcaatg tcgcgtatca tttgtgccgc catttgcacg aagaaggagc gaaactcatc    600

gtgactgaca tcaacaagga agtggtggcg cgcgcggtcg aggaattcgg agcgaaagcg    660

gtcgacccga acgacattta cggcgtggag tgcgacattt ttgctccatg cgcgctcggc    720

ggcatcatca acgatcaaac gattccgcaa ctgaaagcga aagtgatcgc cggatcggca    780

gacaaccagc tgaaagagcc gcgccatggc gacatcatcc atgaaatggg catcgtctat    840

gccccggatt atgtgatcaa cgccggcggc gtcatcaacg tcgcggacga actgtacggc    900

tacaatcggg aacgggcgat gaaaaaaatc gagcaaattt atgacaacat cgaaaaagtg    960

tttgccatcg ccaagcgcga caacattcca acgtatgtgg ccgccgaccg gatggcggaa   1020

gaacggattg aaacgatgcg caaagcgcgc agtccatttt tgcaaaatgg tcaccatatt   1080

ttaagccgcc gtcgcgcccg ctaa                                          1104


<210> SEQ ID NO 2
<211> LENGTH: 367
<212> TYPE: PRT
<213> ORGANISM: Geobacillus stearothermophilus

<400> SEQUENCE: 2

Met Glu Leu Phe Lys Tyr Met Glu Thr Tyr Asp Tyr Glu Gln Val Leu
1               5                   10                  15

Phe Cys Gln Asp Lys Glu Ser Gly Leu Lys Ala Ile Ile Ala Ile His
            20                  25                  30

Asp Thr Thr Leu Gly Pro Ala Leu Gly Gly Thr Arg Met Trp Met Tyr
        35                  40                  45

Asn Ser Glu Glu Glu Ala Leu Glu Asp Ala Leu Arg Leu Ala Arg Gly
    50                  55                  60

Met Thr Tyr Lys Asn Ala Ala Ala Gly Leu Asn Leu Gly Gly Gly Lys
65                  70                  75                  80
```

```
Thr Val Ile Ile Gly Asp Pro Arg Lys Asp Lys Asn Glu Ala Met Phe
                85                  90                  95

Arg Ala Phe Gly Arg Phe Ile Gln Gly Leu Asn Gly Arg Tyr Ile Thr
            100                 105                 110

Ala Glu Asp Val Gly Thr Thr Val Ala Asp Met Asp Ile Ile Tyr Gln
        115                 120                 125

Glu Thr Asp Tyr Val Thr Gly Ile Ser Pro Glu Phe Gly Ser Ser Gly
    130                 135                 140

Asn Pro Ser Pro Ala Thr Ala Tyr Gly Val Tyr Arg Gly Met Lys Ala
145                 150                 155                 160

Ala Ala Lys Glu Ala Phe Gly Ser Asp Ser Leu Glu Gly Lys Val Val
                165                 170                 175

Ala Val Gln Gly Val Gly Asn Val Ala Tyr His Leu Cys Arg His Leu
            180                 185                 190

His Glu Glu Gly Ala Lys Leu Ile Val Thr Asp Ile Asn Lys Glu Val
        195                 200                 205

Val Ala Arg Ala Val Glu Glu Phe Gly Ala Lys Ala Val Asp Pro Asn
    210                 215                 220

Asp Ile Tyr Gly Val Glu Cys Asp Ile Phe Ala Pro Cys Ala Leu Gly
225                 230                 235                 240

Gly Ile Ile Asn Asp Gln Thr Ile Pro Gln Leu Lys Ala Lys Val Ile
                245                 250                 255

Ala Gly Ser Ala Asp Asn Gln Leu Lys Glu Pro Arg His Gly Asp Ile
            260                 265                 270

Ile His Glu Met Gly Ile Val Tyr Ala Pro Asp Tyr Val Ile Asn Ala
        275                 280                 285

Gly Gly Val Ile Asn Val Ala Asp Glu Leu Tyr Gly Tyr Asn Arg Glu
    290                 295                 300

Arg Ala Met Lys Lys Ile Glu Gln Ile Tyr Asp Asn Ile Glu Lys Val
305                 310                 315                 320

Phe Ala Ile Ala Lys Arg Asp Asn Ile Pro Thr Tyr Val Ala Ala Asp
                325                 330                 335

Arg Met Ala Glu Glu Arg Ile Glu Thr Met Arg Lys Ala Arg Ser Pro
            340                 345                 350

Phe Leu Gln Asn Gly His His Ile Leu Ser Arg Arg Arg Ala Arg
        355                 360                 365
```

<210> SEQ ID NO 3
<211> LENGTH: 1095
<212> TYPE: DNA
<213> ORGANISM: Lysinibacillus sphaericus

<400> SEQUENCE: 3

```
atggaaatct tcaagtatat ggaaaagtat gattatgaac aattggtatt ttgccaagac      60

gaagcatctg ggttaaaagc gattatcgct atccatgaca caacacttgg accagcatta     120

ggtggtgctc gtatgtggac ctacgcgaca gaagaaaatg cgattgagga tgcattaaga     180

ttagcacgcg ggatgacata taaaaatgca gctgctggtt taaaccttgg cggtggaaaa     240

acggtcatta ttggggaccc atttaaagat aaaaacgaag aaatgttccg tgctttaggt     300

cgtttcattc aaggattaaa cggtcgctat attaccgctg aagatgttgg tacaaccgta     360

acagatatgg atttaatcca tgaggaaaca aattacgtta caggtatatc gccagcgttt     420

ggttcatcgg gtaatccttc accagtaact gcttatggcg tttatcgtgg catgaaagca     480
```

-continued

```
gcggcgaaag aagcatttgg tacggatatg ctagaaggtc gtactatatc ggtacaaggg    540

ctaggaaacg tagcttacaa gctttgcgag tatttacata atgaaggtgc aaaacttgta    600

gtaacagata ttaaccaagc ggctattgat cgtgttgtca atgattttgg cgctacagca    660

gttgcacctg atgaaatcta ttcacaagaa gtcgatattt tctcaccgtg tgcacttggc    720

gcaattttaa atgacgaaac gattccgcaa ttaaaagcaa aagttattgc tggttctgct    780

aataaccaac tacaagattc acgacatgga gattatttac acgagctagg cattgtttat    840

gcacctgact atgtcattaa tgcaggtggt gtaataaatg tcgcggacga attatatggc    900

tataatcgtg aacgagcgtt gaaacgtgta gatggtattt acgatagtat tgaaaaaatc    960

tttgaaattt ccaaacgtga tagtattcca acatatgttg cggcaaatcg tttggcagaa   1020

gaacgtattg ctcgtgtagc gaaatcgcgt agtcagttct taaaaaatga aaaaaatatt   1080

ttgaacggcc gttaa                                                    1095
```

<210> SEQ ID NO 4
<211> LENGTH: 364
<212> TYPE: PRT
<213> ORGANISM: Lysinibacillus sphaericus

<400> SEQUENCE: 4

```
Met Glu Ile Phe Lys Tyr Met Glu Lys Tyr Asp Tyr Glu Gln Leu Val
1               5                   10                  15

Phe Cys Gln Asp Glu Ala Ser Gly Leu Lys Ala Ile Ile Ala Ile His
            20                  25                  30

Asp Thr Thr Leu Gly Pro Ala Leu Gly Gly Ala Arg Met Trp Thr Tyr
        35                  40                  45

Ala Thr Glu Glu Asn Ala Ile Glu Asp Ala Leu Arg Leu Ala Arg Gly
    50                  55                  60

Met Thr Tyr Lys Asn Ala Ala Ala Gly Leu Asn Leu Gly Gly Gly Lys
65                  70                  75                  80

Thr Val Ile Ile Gly Asp Pro Phe Lys Asp Lys Asn Glu Glu Met Phe
                85                  90                  95

Arg Ala Leu Gly Arg Phe Ile Gln Gly Leu Asn Gly Arg Tyr Ile Thr
            100                 105                 110

Ala Glu Asp Val Gly Thr Thr Val Thr Asp Met Asp Leu Ile His Glu
        115                 120                 125

Glu Thr Asn Tyr Val Thr Gly Ile Ser Pro Ala Phe Gly Ser Ser Gly
    130                 135                 140

Asn Pro Ser Pro Val Thr Ala Tyr Gly Val Tyr Arg Gly Met Lys Ala
145                 150                 155                 160

Ala Ala Lys Glu Ala Phe Gly Thr Asp Met Leu Glu Gly Arg Thr Ile
                165                 170                 175

Ser Val Gln Gly Leu Gly Asn Val Ala Tyr Lys Leu Cys Glu Tyr Leu
            180                 185                 190

His Asn Glu Gly Ala Lys Leu Val Val Thr Asp Ile Asn Gln Ala Ala
        195                 200                 205

Ile Asp Arg Val Val Asn Asp Phe Gly Ala Thr Ala Val Ala Pro Asp
    210                 215                 220

Glu Ile Tyr Ser Gln Glu Val Asp Ile Phe Ser Pro Cys Ala Leu Gly
225                 230                 235                 240

Ala Ile Leu Asn Asp Glu Thr Ile Pro Gln Leu Lys Ala Lys Val Ile
                245                 250                 255
```

-continued

```
Ala Gly Ser Ala Asn Asn Gln Leu Gln Asp Ser Arg His Gly Asp Tyr
            260                 265                 270

Leu His Glu Leu Gly Ile Val Tyr Ala Pro Asp Tyr Val Ile Asn Ala
        275                 280                 285

Gly Gly Val Ile Asn Val Ala Asp Glu Leu Tyr Gly Tyr Asn Arg Glu
    290                 295                 300

Arg Ala Leu Lys Arg Val Asp Gly Ile Tyr Asp Ser Ile Glu Lys Ile
305                 310                 315                 320

Phe Glu Ile Ser Lys Arg Asp Ser Ile Pro Thr Tyr Val Ala Ala Asn
                325                 330                 335

Arg Leu Ala Glu Glu Arg Ile Ala Arg Val Ala Lys Ser Arg Ser Gln
            340                 345                 350

Phe Leu Lys Asn Glu Lys Asn Ile Leu Asn Gly Arg
        355                 360
```

<210> SEQ ID NO 5
<211> LENGTH: 1101
<212> TYPE: DNA
<213> ORGANISM: Bacillus cereus

<400> SEQUENCE: 5

```
atgacattag aaatcttcga atacttagaa aaatatgatt atgagcaagt agtattttgt      60

caagataaag aatctggttt aaaagcaatt attgcaattc atgatacaac acttggaccg     120

gctcttggtg gaacaagaat gtggacatat gattctgaag aagcggcgat tgaagatgca     180

ttgcgtcttg caaaagggat gacatacaaa aacgcagcag ctggtttaaa cttaggtggt     240

gcgaaaacag taattatcgg tgatcctcgt aaagataaga gcgaagcaat gttccgtgca     300

ctaggacgtt atatccaagg actaaacgga cgttacatta cagctgaaga tgttggtaca     360

acagtagatg atatggatat tatccatgaa gaaactgact ttgtaacagg tatctcacca     420

tcattcggtt cttctggtaa cccatctccg gtaactgcat acggtgttta ccgtggtatg     480

aaagcagctg caaaagaagc tttcggtact gacaatttag aaggaaaagt aattgctgtt     540

caaggcgttg gtaacgtagc atatcaccta tgcaaacatt tacacgctga aggagcaaaa     600

ttaattgtta cagatattaa taaagaagct gtacaacgtg ctgtagaaga attcggtgca     660

tcagcagttg aaccaaatga aatttacggt gttgaatgcg atatttacgc accatgtgca     720

ctaggcgcaa cagttaatga tgaaactatt ccacaactta aagcaaaagt aatcgcaggt     780

tctgcgaata accaattaaa agaagatcgt catggtgaca tcattcatga aatgggtatt     840

gtatacgcac cagattatgt aattaatgca ggtggcgtaa ttaacgtagc agacgaatta     900

tatggataca atagagaacg tgcactaaaa cgtgttgagt ctatttatga cacgattgca     960

aaagtaatcg aaatttcaaa acgcgatggc atagcaactt atgtagcggc agatcgtcta    1020

gctgaagagc gcattgcaag cttgaagaat tctcgtagca cttacttacg caacggtcac    1080

gatattatta gccgtcgcta a                                                1101
```

<210> SEQ ID NO 6
<211> LENGTH: 366
<212> TYPE: PRT
<213> ORGANISM: Bacillus cereus

<400> SEQUENCE: 6

```
Met Thr Leu Glu Ile Phe Glu Tyr Leu Glu Lys Tyr Asp Tyr Glu Gln
1               5                   10                  15
```

-continued

```
Val Val Phe Cys Gln Asp Lys Glu Ser Gly Leu Lys Ala Ile Ile Ala
            20                  25                  30

Ile His Asp Thr Thr Leu Gly Pro Ala Leu Gly Gly Thr Arg Met Trp
        35                  40                  45

Thr Tyr Asp Ser Glu Glu Ala Ala Ile Glu Asp Ala Leu Arg Leu Ala
    50                  55                  60

Lys Gly Met Thr Tyr Lys Asn Ala Ala Ala Gly Leu Asn Leu Gly Gly
65                  70                  75                  80

Ala Lys Thr Val Ile Ile Gly Asp Pro Arg Lys Asp Lys Ser Glu Ala
                85                  90                  95

Met Phe Arg Ala Leu Gly Arg Tyr Ile Gln Gly Leu Asn Gly Arg Tyr
            100                 105                 110

Ile Thr Ala Glu Asp Val Gly Thr Thr Val Asp Asp Met Asp Ile Ile
        115                 120                 125

His Glu Glu Thr Asp Phe Val Thr Gly Ile Ser Pro Ser Phe Gly Ser
    130                 135                 140

Ser Gly Asn Pro Ser Pro Val Thr Ala Tyr Gly Val Tyr Arg Gly Met
145                 150                 155                 160

Lys Ala Ala Ala Lys Glu Ala Phe Gly Thr Asp Asn Leu Glu Gly Lys
                165                 170                 175

Val Ile Ala Val Gln Gly Val Gly Asn Val Ala Tyr His Leu Cys Lys
            180                 185                 190

His Leu His Ala Glu Gly Ala Lys Leu Ile Val Thr Asp Ile Asn Lys
        195                 200                 205

Glu Ala Val Gln Arg Ala Val Glu Glu Phe Gly Ala Ser Ala Val Glu
    210                 215                 220

Pro Asn Glu Ile Tyr Gly Val Glu Cys Asp Ile Tyr Ala Pro Cys Ala
225                 230                 235                 240

Leu Gly Ala Thr Val Asn Asp Glu Thr Ile Pro Gln Leu Lys Ala Lys
                245                 250                 255

Val Ile Ala Gly Ser Ala Asn Asn Gln Leu Lys Glu Asp Arg His Gly
            260                 265                 270

Asp Ile Ile His Glu Met Gly Ile Val Tyr Ala Pro Asp Tyr Val Ile
        275                 280                 285

Asn Ala Gly Gly Val Ile Asn Val Ala Asp Glu Leu Tyr Gly Tyr Asn
    290                 295                 300

Arg Glu Arg Ala Leu Lys Arg Val Glu Ser Ile Tyr Asp Thr Ile Ala
305                 310                 315                 320

Lys Val Ile Glu Ile Ser Lys Arg Asp Gly Ile Ala Thr Tyr Val Ala
                325                 330                 335

Ala Asp Arg Leu Ala Glu Glu Arg Ile Ala Ser Leu Lys Asn Ser Arg
            340                 345                 350

Ser Thr Tyr Leu Arg Asn Gly His Asp Ile Ile Ser Arg Arg
        355                 360                 365
```

<210> SEQ ID NO 7
<211> LENGTH: 1095
<212> TYPE: DNA
<213> ORGANISM: Bacillus licheniformis

<400> SEQUENCE: 7

```
atggaactat ttcgatatat ggaacagtat gactacgagc aattggtatt ttgccaagat      60

aaacagtccg gtttaaaagc gatcatcgcg attcatgata cgacgctcgg gccggctctc     120

ggcggcacaa gaatgtggac atacgaaagt gaagaagccg caattgaaga tgcgctgcgc     180
```

```
cttgcgcggg gaatgaccta caaaaatgcg gcggccggac tgaacctcgg aggaggcaaa    240

accgttatta tcggagatcc gcgcaaagat aaaaacgaag aaatgttccg cgctttcggc    300

cgctacattc aaggcttgaa cggcagatac atcacagccg aagacgtcgg tacaaccgtt    360

gaagatatgg acatcattca tgacgaaacc gatttcgtta caggcatttc acctgctttc    420

ggttcatcag gaaatccttc tccggtaaca gcttacgggg tatataaagg gatgaaggcg    480

gcggcgaaag cggcattcgg aacggattcg cttgaaggca aaaccgttgc ggttcaaggc    540

gtcggaaacg tggcctacaa cctgtgccgg cacctccacg aagaaggcgc gaaactgatc    600

gtgaccgaca tcaacaaaga agcagttgaa cgtgcagtcg ccgaattcgg cgcccgcgcc    660

gtcgatccgg atgatattta ttcgcaggaa tgcgatatat atgcgccgtg tgccctcgga    720

gcgacaatca acgatgatac gattccgcag ctgaaagcca aagtgattgc cggggcagcc    780

aacaaccagc tgaaagaaac ccgccacggt gatcaaatcc acgacatggg catcgtttat    840

gccccggact atgtcatcaa tgccggcggc gtcatcaatg tcgctgacga gctttacggc    900

tataattcgg agcgcgcgct gaagaaagtc gaaggcatct acggaaacat tgaacgcgtc    960

cttgaaattt cgaagcgcga ccgcattccg acatacttgg ccgcagaccg tctggcggaa   1020

gaacgaattg agcgcatgcg ccaatcgaga agccaatttt tgcaaaacgg ccatcacatt   1080

ttaagcagac gttaa                                                    1095
```

<210> SEQ ID NO 8
<211> LENGTH: 364
<212> TYPE: PRT
<213> ORGANISM: Bacillus licheniformis

<400> SEQUENCE: 8

```
Met Glu Leu Phe Arg Tyr Met Glu Gln Tyr Asp Tyr Glu Gln Leu Val
1               5                   10                  15

Phe Cys Gln Asp Lys Gln Ser Gly Leu Lys Ala Ile Ile Ala Ile His
            20                  25                  30

Asp Thr Thr Leu Gly Pro Ala Leu Gly Gly Thr Arg Met Trp Thr Tyr
        35                  40                  45

Glu Ser Glu Glu Ala Ala Ile Glu Asp Ala Leu Arg Leu Ala Arg Gly
    50                  55                  60

Met Thr Tyr Lys Asn Ala Ala Ala Gly Leu Asn Leu Gly Gly Gly Lys
65                  70                  75                  80

Thr Val Ile Ile Gly Asp Pro Arg Lys Asp Lys Asn Glu Glu Met Phe
                85                  90                  95

Arg Ala Phe Gly Arg Tyr Ile Gln Gly Leu Asn Gly Arg Tyr Ile Thr
            100                 105                 110

Ala Glu Asp Val Gly Thr Thr Val Glu Asp Met Asp Ile Ile His Asp
        115                 120                 125

Glu Thr Asp Phe Val Thr Gly Ile Ser Pro Ala Phe Gly Ser Ser Gly
    130                 135                 140

Asn Pro Ser Pro Val Thr Ala Tyr Gly Val Tyr Lys Gly Met Lys Ala
145                 150                 155                 160

Ala Ala Lys Ala Ala Phe Gly Thr Asp Ser Leu Glu Gly Lys Thr Val
                165                 170                 175

Ala Val Gln Gly Val Gly Asn Val Ala Tyr Asn Leu Cys Arg His Leu
            180                 185                 190

His Glu Glu Gly Ala Lys Leu Ile Val Thr Asp Ile Asn Lys Glu Ala
        195                 200                 205
```

-continued

```
Val Glu Arg Ala Val Ala Glu Phe Gly Ala Arg Ala Val Asp Pro Asp
    210                 215                 220

Asp Ile Tyr Ser Gln Glu Cys Asp Ile Tyr Ala Pro Cys Ala Leu Gly
225                 230                 235                 240

Ala Thr Ile Asn Asp Asp Thr Ile Pro Gln Leu Lys Ala Lys Val Ile
                245                 250                 255

Ala Gly Ala Ala Asn Asn Gln Leu Lys Glu Thr Arg His Gly Asp Gln
            260                 265                 270

Ile His Asp Met Gly Ile Val Tyr Ala Pro Asp Tyr Val Ile Asn Ala
        275                 280                 285

Gly Gly Val Ile Asn Val Ala Asp Glu Leu Tyr Gly Tyr Asn Ser Glu
    290                 295                 300

Arg Ala Leu Lys Lys Val Glu Gly Ile Tyr Gly Asn Ile Glu Arg Val
305                 310                 315                 320

Leu Glu Ile Ser Lys Arg Asp Arg Ile Pro Thr Tyr Leu Ala Ala Asp
                325                 330                 335

Arg Leu Ala Glu Glu Arg Ile Glu Arg Met Arg Gln Ser Arg Ser Gln
            340                 345                 350

Phe Leu Gln Asn Gly His His Ile Leu Ser Arg Arg
        355                 360


<210> SEQ ID NO 9
<211> LENGTH: 32
<212> TYPE: DNA
<213> ORGANISM: Artificial Sequence
<220> FEATURE:
<223> OTHER INFORMATION: Sense primer for preparing a mutated leucine
      dehydrogenase

<400> SEQUENCE: 9

gactatgtca ccggccgttc gcccgaattc gg                                32


<210> SEQ ID NO 10
<211> LENGTH: 32
<212> TYPE: DNA
<213> ORGANISM: Artificial Sequence
<220> FEATURE:
<223> OTHER INFORMATION: Antisense primer for preparing a mutated
      leucine dehydrogenase

<400> SEQUENCE: 10

ccgaattcgg gcgaacggcc ggtgacatag tc                                32
```

MODIFIED LEUCINE DEHYDROGENASE

This application is a continuation of, and claims priority under 35 U.S.C. §120 to, International Patent Application No. PCT/JP2013/059124, filed on Mar. 27, 2013, which claims priority therethrough under 35 U.S.C. §119 to Japanese Patent Application No. 2012-082777, filed on Mar. 30, 2012, which are incorporated in their entireties by reference. Also, the Sequence Listing filed electronically herewith is hereby incorporated by reference (File name: 2014-09-19T_US-522_Seq_List; File size: 20 KB; Date recorded: Sep. 19, 2014).

FIELD OF THE INVENTION

The present invention related to a modified leucine dehydrogenase, a method of analyzing total branched-chain amino acids using the same, and the like.

BRIEF DESCRIPTION OF THE RELATED ART

It is known that some amino acids can become indicators for various health conditions. In particular, branched-chain amino acids (BCAA: L-leucine, L-isoleucine and L-valine) are important amino acids that are abundant in various biological samples, foods, and beverages. The branched-chain amino acids are abundant in muscle in living bodies and are known as a marker of protein nutrition. It is known that concentrations of the branched-chain amino acids in blood are reduced in patients with hepatic cirrhosis or hepatic encephalopathy, and indicators such as Fisher ratio and BTR value are utilized for health condition and follow-up of the liver.

Methods using analytical instruments, including high-performance liquid chromatography (HPLC) and LC-MS, are widely used to analyze amino acids. When measuring total branched-chain amino acids, an enzymatic kit for measuring the BTR value utilizing leucine dehydrogenase (e.g., Japanese patent application laid-open publication no. JP 2007-289096-A) and a biosensor for electrochemically measuring the total branched-chain amino acids utilizing leucine dehydrogenase (e.g., International Publication no. WO2005/075970) have been reported.

SUMMARY OF THE INVENTION

There are several points that could be improved in the measurement of concentrations of the total branched-chain amino acids using a leucine dehydrogenase.

For example, concentration of the total branched-chain amino acids is measured using a leucine dehydrogenase in an enzymatic kit. However, these methods typically are performed until an endpoint is reached at which the substrates are fully and completely reacted. This is because substrate specificities (reaction rates) of the leucine dehydrogenase for L-leucine, L-isoleucine and L-valine are each different. For wild-type leucine dehydrogenase, the substrate specificities for L-isoleucine and L-valine are lower than that for L-leucine and therefore the reaction rates for L-isoleucine and L-valine are slower than that for L-leucine. Therefore, existing methods have the disadvantage that it takes a long time to measure the concentration of the total branched-chain amino acids in the enzymatic kit using the leucine dehydrogenase due to the longer reaction rates of L-isoleucine and L-valine.

In addition, when a plurality of amino acids that are the substrates of the leucine dehydrogenase are present, each concentration of branched-chain amino acids cannot be independently measured with the biosensor. This is because the leucine dehydrogenase reacts not only with L-leucine but also with L-isoleucine and L-valine. In the case as above, a total concentration of the branched-chain amino acids could also not be measured in general. This is because the substrate specificities (reaction rates) of the leucine dehydrogenase for L-leucine, L-isoleucine and L-valine are different from each other.

As a result of an extensive study, the present inventors have conceived that a concentration of total branched-chain amino acids may be measured utilizing a rating method (initial rate method) by enhancing an activity of a leucine dehydrogenase for each amino acid of branched-chain amino acids, particularly for L-isoleucine and L-valine, or the like, to improve substrate specificities of the leucine dehydrogenase for the branched-chain amino acids, in order to rapidly measure the concentration of the total branched-chain amino acids, and have succeeded in developing a modified leucine dehydrogenase that ha improved substrate specificities for the branched-chain amino acids. The present inventors have also succeeded in improving other properties of the leucine dehydrogenase that are associated with the measurement of the concentration of the total branched-chain amino acids.

It is an aspect of the present invention to provide a modified leucine dehydrogenase enzyme comprising at least one amino acid mutation as compared to a non-modified leucine dehydrogenase enzyme, wherein said modified leucine dehydrogenase is improved in one or more properties selected from the group consisting of:

(a) substrate specificities for total branched-chain amino acids;

(b) activity for any branched-chain amino acid;

(c) thermal stability; and (d) combinations thereof.

It is a further aspect of the present invention to provide the modified leucine dehydrogenase enzyme as described above, wherein the mutation is a substitution of isoleucine in a TGI motif in an amino acid sequence of the non-modified leucine dehydrogenase enzyme.

It is a further aspect of the present invention to provide the modified leucine dehydrogenase enzyme as described above, wherein the isoleucine in the TGI motif is substituted with an amino acid selected from the group consisting of methionine, arginine, histidine, phenylalanine, leucine, lysine, cysteine, tyrosine, alanine, glycine, serine, asparagine, and tryptophan.

It is a further aspect of the present invention to provide the modified leucine dehydrogenase enzyme as described above, wherein the mutation is a substitution of isoleucine in a GVI motif in an amino acid sequence of the non-modified leucine dehydrogenase enzyme.

It is a further aspect of the present invention to provide the modified leucine dehydrogenase enzyme as described above, wherein the isoleucine in the GVI motif is substituted with an amino acid selected from the group consisting of phenylalanine, histidine, asparagine, tyrosine, leucine, lysine, glutamine, arginine, aspartic acid, threonine, glutamic acid, serine, cysteine, alanine, glycine, valine, tryptophan, and methionine.

It is a further aspect of the present invention to provide the modified leucine dehydrogenase enzyme as described above, wherein the non-modified leucine dehydrogenase enzyme is derived from *Geobacillus stearothermophilus.*

It is a further aspect of the present invention to provide the modified leucine dehydrogenase enzyme as described above, comprising a protein selected from the group consisting of:

(A) a protein comprising the amino acid sequence of SEQ ID NO: 2, but having a substitution of isoleucine in the TGI motif with an amino acid residue selected from the group consisting of methionine, arginine, histidine, phenylalanine, leucine, lysine, cysteine, tyrosine, alanine, glycine, serine, asparagine, or tryptophan;

(B) a protein comprising the amino acid sequence of SEQ ID NO: 2, but having a substitution of isoleucine in the GVI motif with an amino acid selected from the group consisting of phenylalanine, histidine, asparagine, tyrosine, leucine, lysine, glutamine, arginine, aspartic acid, threonine, glutamic acid, serine, cysteine, alanine, glycine, valine, tryptophan, and methionine;

(C) a protein comprising the amino acid sequence of SEQ ID NO: 2, but having a substitution of isoleucine in the TGI motif with an amino acid selected from the group consisting of methionine, arginine, histidine, phenylalanine, leucine, lysine, cysteine, tyrosine, alanine, glycine, serine, asparagine, and tryptophan, and a substitution of isoleucine in the GVI motif with an amino acid selected from the group consisting of phenylalanine, histidine, asparagine, tyrosine, leucine, lysine, glutamine, arginine, aspartic acid, threonine, glutamic acid, serine, cysteine, alanine, glycine, valine, tryptophan, and methionine, and (D) a protein as described in (A), (B), or (C) above, but also comprising one or several additional mutations of amino acid residues, and having one or more improved properties selected from the group consisting of:

(a) substrate specificities for total branched-chain amino acids;

(b) activity for any branched-chain amino acid; and (c) thermal stability.

It is a further aspect of the present invention to provide a method of analyzing total branched-chain amino acids, comprising measuring the total branched-chain amino acids contained in a test sample using the modified leucine dehydrogenase enzyme as described above.

It is a further aspect of the present invention to provide the method as described above, comprising mixing the test sample with nicotinamide adenine dinucleotide ($NAD^+$) and detecting NADH formed from $NAD^+$ by an action of the modified leucine dehydrogenase enzyme.

It is a further aspect of the present invention to provide a method of producing a derivative of a branched-chain amino acid, comprising forming the derivative from the branched-chain amino acid using the modified leucine dehydrogenase enzyme as described above.

It is a further aspect of the present invention to provide a polynucleotide encoding the modified leucine dehydrogenase enzyme as described above.

It is a further aspect of the present invention to provide an expression vector comprising the polynucleotide as described above.

It is a further aspect of the present invention to provide a transformant comprising the expression vector as described above.

It is a further aspect of the present invention to provide a method of producing a modified enzyme in which at least one amino acid residue is mutated so as to improve a property of a leucine dehydrogenase which is associated with measurement of total branched-chain amino acids, comprising forming the modified enzyme using the transformant as described above.

It is a further aspect of the present invention to provide a kit for analyzing total branched-chain amino acids, comprising the modified enzyme as described above.

It is a further aspect of the present invention to provide the kit for as described above, further comprising at least one of a buffer solution or a buffer salt for a reaction and nicotinamide adenine dinucleotide ($NAD^+$).

It is a further aspect of the present invention to provide an enzyme sensor for analyzing total branched-chain amino acids, comprising (a) an electrode for detection and (b) the modified leucine dehydrogenase enzyme as described above, which is immobilized or retained on the electrode for detection.

The modified enzyme of the present invention is useful for rapid measurement of concentration of total branched-chain amino acids with improved substrate specificity. The modified enzyme of the present invention is also useful for measurement of any branched-chain amino acid and/or production of derivatives of any branched-chain amino acid (e.g., 2-oxo-derivative) because its activity for the branched-chain amino acids is enhanced. The modified enzyme of the present invention is also excellent in stability because it is excellent in thermal stability in an aqueous solution. Therefore the modified enzyme of the present invention is useful particularly as a liquid reagent. The analysis method of the present invention is useful for diagnosis of diseases such as hepatic cirrhosis, hepatic encephalopathy, and the like.

DESCRIPTION OF THE PREFERRED EMBODIMENTS

The present invention provides a modified enzyme. The modified enzyme of the present invention can be one in which at least one amino acid residue in a leucine dehydrogenase is mutated so as to improve a property of the leucine dehydrogenase, which is associated with the measurement of total branched-chain amino acids.

Examples of the mutation of the amino acid residue may include substitution, deletion, addition and insertion, and the substitution is preferred particular example.

Amino acid residues to be mutated include L-alanine (A), L-asparagine (N), L-cysteine (C), L-glutamine (Q), glycine (G), L-isoleucine (I), L-leucine (L), L-methionine (M), L-phenylalanine (F), L-proline (P), L-serine (S), L-threonine (T), L-tryptophan (W), L-tyrosine (Y), L-valine (V), L-aspartic acid (D), L-glutamic acid (E), L-arginine (R), L-histidine (H) or L-lysine (K), and may be a naturally occurring L-α-amino acid. When the mutation is substitution, addition or insertion, the amino acid residue to be substituted, added or inserted can be the same as the amino acid residue to be mutated as described above.

The branched-chain amino acids ("BCAA") include naturally occurring L-α-amino acids having a branched chain as a side chain, and specifically include L-leucine, L-isoleucine, and L-valine. The branched-chain amino acids (i.e., L-leucine, L-isoleucine and L-valine) are collectively measured in the measurement of the total branched-chain amino acids. The leucine dehydrogenase is an oxidoreductase that catalyzes the following reaction (EC 1.4.1.9).

$$\text{L-leucine}+H_2O+NAD^+\rightarrow\text{4-methyl-2-oxopentanoic acid}+NH_3+NADH+H^+$$

Figure 1:
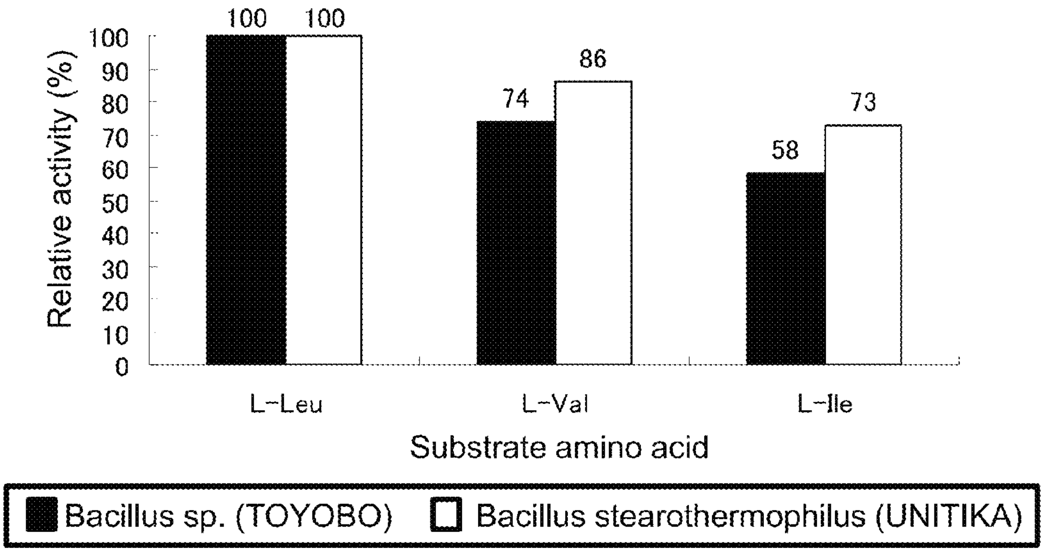
FIG. 1 shows substrate specificities of each wild-type leucine dehydrogenase for each branched-chain amino acid (L-leucine, L-isoleucine and L-valine)

It is known that although a wild-type leucine dehydrogenase acts upon not only L-leucine, but also on L-isoleucine and L-valine; although its activities for L-isoleucine and L-valine are lower than that for L-leucine. The substrate specificities of the wild-type leucine dehydrogenases derived from *Bacillus* sp. and *Geobacillus stearothermophilus* for L-leucine, L-isoleucine and L-valine are shown in FIG. 1 as relative activities when the relative activities for L-leucine are regarded as 100. As shown in FIG. 1, the activities of the wild-type leucine dehydrogenases are relatively low for the branched-chain amino acids other than L-leucine, and in particular, the relative activities for L-isoleucine are 75 or less relative to the activities for L-leucine.

Wild-type leucine dehydrogenase derived from any organism, such as microorganisms such as bacteria, actinomycetes and fungi, as well as insects, fish, animals and plants, can be used to derive the modified enzyme of the present invention. Examples of the wild-type leucine dehydrogenase may include those derived from organisms belonging to the genus *Bacillus* and genera related thereto. Examples of the genera related to the genus *Bacillus* may include the genus *Geobacillus*, the genus *Paenibacillus* and the genus *Oceanobacillus*. The genera related to the genus *Bacillus* belong to Bacillaceae, as is similar to the genus *Bacillus.*

Examples of the microorganisms belonging to the genus *Bacillus* and the genera related thereto may include *Bacillus sphaericus, Bacillus cereus, Bacillus licheniformis, Bacillus* sp., and *Geobacillus stearothermophilus.*

The position at which a mutation is introduced in the wild-type leucine dehydrogenase can be a position located in close proximity to an active center of the leucine dehydrogenase. A person skilled in the art can align an amino acid sequence of the leucine dehydrogenase derived from *Geobacillus stearothermophilus* with an amino acid sequence of another leucine dehydrogenase, and thus can easily determine an amino acid residue position located in close proximity to an active center of the wild-type leucine dehydrogenases derived from organisms other than *Geobacillus stearothermophilus.*

In addition, results of analyzing three-dimensional structures have been reported for leucine dehydrogenases (see, e.g., Baker et al., Structure 3: 693-705 (1995)). Therefore, a person skilled in the art can also easily specify the amino acid residue located in close proximity of an active center of the leucine dehydrogenases derived from organisms other than *Geobacillus stearothermophilus*, based on the results of analyzing three-dimensional structure.

In a particular embodiment, a mutation that results in the improvement of the property of the leucine dehydrogenase associated with the measurement of the total branched-chain amino acids can be a substitution of isoleucine (I) in a TGI motif in the wild-type leucine dehydrogenase. The TGI motif is composed of the three consecutive amino acid residues threonine (T)-glycine (G)-isoleucine (I). The position of the TGI motif in the amino acid sequence of the wild-type leucine dehydrogenase may be different depending on the origin of the enzyme. However, a person skilled in the art can appropriately determine the position of the TGI motif in the amino acid sequence of the wild-type leucine dehydrogenase, and thus can specify the position of isoleucine (I) to be substituted. Generally, in the amino acid sequence of the wild-type leucine dehydrogenase, the TGI motif is located within an amino acid region of positions 134 to 138 and the isoleucine (I) is located at positions 136 to 138 (see, e.g., Table 1).

TABLE 1

Position of TGI motif in leucine dehydrogenase

| Leucine dehydrogenase | Position | | SEQ ID NO (sequence of wild-type enzyme | |
|---|---|---|---|---|
| | TGI motif | Ile | Nucleotide sequence | Amino acid sequence |
| *G. stearothermophilus* | 134-136 | 136 | 1 | 2 |
| *B. sphaericus* | 134-136 | 136 | 3 | 4 |
| *B. cereus* | 136-138 | 138 | 5 | 6 |
| *B. licheniformis* | 134-136 | 136 | 7 | 8 |

In another particular embodiment, a mutation that results in the improvement of the property of the leucine dehydrogenase associated with the measurement of the total branched-chain amino acids is a substitution of isoleucine (I) in a GVI motif of the wild-type leucine dehydrogenase. The GVI motif is composed of the three consecutive amino acid residues of glycine (G)-valine (V)-isoleucine (I). The position of the GVI motif in the amino acid sequence of the wild-type leucine dehydrogenase may be different depending on the origin of the enzyme. However, a person skilled in the art can appropriately determine the position of the GVI motif in the amino acid sequence of the wild-type leucine dehydrogenase, and thus can specify the position of isoleucine (I) to be substituted. Generally, in the amino acid sequence of the wild-type leucine dehydrogenase, the GVI motif is located within an amino acid region at positions 290 to 294, and isoleucine (I) is located at positions 292 to 294 (see, e.g., Table 2). The modified enzyme of the present invention may further have the above substitution of isoleucine (I) in the TGI motif in addition to the substitution of isoleucine (I) in the GVI motif as the mutations to improve the property of the leucine dehydrogenase associated with the measurement of the total branched-chain amino acids.

TABLE 2

Position of GVI motif in leucine dehydrogenase

| Leucine dehydrogenase | Position | | SEQ ID NO (sequence of wild- type enzyme) | |
|---|---|---|---|---|
| | GVI motif | Ile | Nucleotide sequence | Amino acid sequence |
| *G. stearothermophilus* | 290-292 | 292 | 1 | 2 |
| *B. sphaericus* | 290-292 | 292 | 3 | 4 |
| *B. cereus* | 292-294 | 294 | 5 | 6 |
| *B. licheniformis* | 290-292 | 292 | 7 | 8 |

The properties of the leucine dehydrogenase which are associated with the measurement of the total branched-chain amino acids may include the following:

(a) substrate specificities of the leucine dehydrogenase for the total branched-chain amino acids;

(b) an activity of the leucine dehydrogenase for any branched-chain amino acid; and (c) a thermal stability of the leucine dehydrogenase.

The modified enzyme of the present invention may have only one of the aforementioned properties, or may have two or three of the aforementioned properties in combination.

For the isoleucine (I) in the TGI motif, examples of the mutation to improve at least one property selected from the properties (a) to (c) may include substitutions with methionine (M), arginine (R), histidine (H), phenylalanine (F), leucine (L), lysine (K), cysteine (C), tyrosine (Y), alanine (A), glycine (G), serine (S), asparagine (N) and tryptophan (W).

For the isoleucine (I) in the GVI motif, examples of the mutation to improve at least one property selected from the properties (a) to (c) may include substitutions with phenylalanine (F), histidine (H), asparagine (N), tyrosine (Y), leucine (L), lysine (K), glutamine (Q), arginine (R), aspartic acid (D), threonine (T), glutamic acid (E), serine (S), cysteine (C), alanine (A), glycine (G), valine (V), tryptophan (W) and methionine (M).

The modified enzyme of the present invention can be used under any pH condition, and is suitably used under a neutral condition and/or an alkaline condition.

The neutral condition under which the modified enzyme of the present invention is suitably used can be any pH condition within the range of pH 6.0 or higher and pH 8.0 or lower. For example, the neutral condition can be any pH condition within the range of pH 7.0 or higher and pH 8.0 or lower (e.g., pH 7.0, pH 7.5 or pH 8.0).

The alkaline condition under which the modified enzyme of the present invention is suitably used refers to any pH condition within the range of more than pH 8.0 and pH 11.0 or lower. An upper limit of a pH range in the alkaline condition can be 10.5 or lower or even 10.0 or lower. For example, the alkaline condition can be any pH condition within the range of pH 8.5 or higher and pH 9.5 or lower (e.g., pH 9.0).

In one embodiment, the substrate specificities of leucine dehydrogenase for the total branched-chain amino acids are improved as the property of the leucine dehydrogenase which is associated with the measurement of the total branched-chain amino acids. The improvement of the substrate specificities of the leucine dehydrogenase for the total branched-chain amino acids are not intended to enhance the substrate specificity of the leucine dehydrogenase for a certain branched-chain amino acid, but refers to making the substrate specificities (reaction rates) for all of the branched-chain amino acids (i.e., L-leucine, L-isoleucine and L-valine) more equivalent. Specifically, the improvement of the substrate specificities of the leucine dehydrogenase for the total branched-chain amino acids can be accomplished when each relative activity of the modified enzyme for isoleucine and valine is closer to 100 compared to each relative activity of the wild-type enzyme for isoleucine and valine, when the relative activity of the leucine dehydrogenase for leucine is regarded as 100. Concerning the substrate specificities of the leucine dehydrogenase for the total branched-chain amino acids, the relative activities of the leucine dehydrogenase for both isoleucine and valine can be 80 or more and 120 or less, 85 or more and 115 or less, 90 or more and 110 or less, or even 95 or more and 105 or less when the relative activity of the leucine dehydrogenase for leucine is regarded as 100. Examples of the modification in the modified enzyme of the present invention in which the relative activities of the leucine dehydrogenase for both isoleucine and valine are 80 or more and 120 or less when the relative activity for leucine is regarded as 100 may include 1) the substitution of isoleucine (I) in the TGI motif with an amino acid residue described below and/or the substitution of isoleucine (I) in the GVI motif with an amino acid residue described below, which is suitable for the improvement of the substrate specificities under the alkaline condition, as well as 2) the substitution of isoleucine (I) in the TGI motif with an amino acid residue described below and/or the substitution of isoleucine (I) in the GVI motif with an amino acid residue described below, which is suitable for the improvement of the property under the neutral condition.

1) Substitution suitable for improvement of substrate specificities under alkaline condition (a) Amino acid residue after substitution at position 136 (alkaline condition)

Methionine (M), arginine (R), phenylalanine (F), lysine (K), cysteine (C), tyrosine (Y), alanine (A), glycine (G) or serine (S)

(b) Amino acid residue after substitution at position 292 (alkaline condition)

Phenylalanine (F), histidine (H), asparagine (N), tyrosine (Y), lysine (K), glutamine (Q), glutamic acid (E) or glycine (G)

2) Substitution suitable for improvement of substrate specificities under neutral condition (c) Amino acid residue after substitution at position 136 (neutral condition)

Alanine (A), glycine (G), histidine (H), lysine (K), leucine (L), serine (S) or tyrosine (Y)

(d) Amino acid residue after substitution at position 292 (neutral condition)

Alanine (A), cysteine (C), aspartic acid (D), glycine (G), lysine (K), leucine (L), methionine (M), arginine (R), serine (S), threonine (T) or valine (V).

In another embodiment, the activity of the leucine dehydrogenase for any branched-chain amino acid is improved as the property of the leucine dehydrogenase which is associated with the measurement of the total branched-chain amino acids. The improvement of the activity of the leucine dehydrogenase for any branched-chain amino acid means that the activity of the modified enzyme for one or more amino acids such as L-leucine, L-isoleucine and L-valine is enhanced relative to the activity of the wild-type enzyme for the same. Specifically, the improvement of the activity of the leucine dehydrogenase for any branched-chain amino acid can be accomplished in the case where the activity of the modified leucine dehydrogenase for any amino acid such as L-leucine, L-isoleucine and L-valine is higher than 100 when the activity of the wild-type leucine dehydrogenase for that amino acid is regarded as 100. Such a modified enzyme enables rapid measurement of an individual branched-chain amino acid, and consequently is useful for the measurement of the total branched-chain amino acids. A level of the enhancement of the activity of the modified enzyme can be 1.3 fold or more, 1.5 fold or more, 1.7 fold or more, or even 2.0 fold or more relative to the activity of the wild-type enzyme. Examples of the modification in the modified enzyme of the present invention having 1.3 fold or more enhancement of the activity relative to the wild-type enzyme may include 1) the substitution of isoleucine (I) in the TGI motif with the following amino acid residue and/or the substitution of isoleucine (I) in the GVI motif with the following amino acid residue, which is suitable for the improvement of the activity under the alkaline condition as well as 2) the substitution of isoleucine (I) in the TGI motif with the following amino acid residue and/or the substitution of isoleucine (I) in the GVI motif with the following amino acid residue, which is suitable for the improvement of the activity under the neutral condition.

1) Substitution suitable for improvement of activity under alkaline condition 1-1) Amino acid residues after substitution at position 136 (under alkaline condition)

(i) Enhancement of the activity for L-leucine (under alkaline condition)

Methionine (M), arginine (R), histidine (H), phenylalanine (F), leucine (L), lysine (K), cysteine (C), tyrosine (Y), alanine (A), glycine (G), serine (S), asparagine (N), or tryptophan (W).

(ii) Enhancement of activity for L-isoleucine (under alkaline condition)

Methionine (M), arginine (R), histidine (H), phenylalanine (F), leucine (L), lysine (K), cysteine (C), tyrosine (Y), alanine (A), glycine (G), serine (S), asparagine (N), or tryptophan (W).

(iii) Enhancement of activity for L-valine (under alkaline condition)

Methionine (M), arginine (R), histidine (H), phenylalanine (F), leucine (L), lysine (K), cysteine (C), tyrosine (Y), alanine (A), glycine (G), serine (S), asparagine (N), or tryptophan (W).

1-2) Amino acid residues after substitution at position 292 (under alkaline condition)

(iv) Enhancement of activity for L-leucine (under alkaline condition)

Phenylalanine (F), histidine (H), asparagine (N), tyrosine (Y), leucine (L), lysine (K), glutamine (Q), arginine (R), aspartic acid (D), threonine (T), glutamic acid (E), serine (S), cysteine (C), alanine (A), or glycine (G).

(v) Enhancement of activity for L-isoleucine (under alkaline condition)

Phenylalanine (F), histidine (H), asparagine (N), tyrosine (Y), leucine (L), lysine (K), glutamine (Q), arginine (R), aspartic acid (D), threonine (T), glutamic acid (E), serine (S), cysteine (C), alanine (A), glycine (G), valine (V), or tryptophan (W).

(vi) Enhancement of activity for L-valine (under alkaline condition)

Phenylalanine (F), histidine (H), asparagine (N), tyrosine (Y), leucine (L), lysine (K), glutamine (Q), arginine (R), aspartic acid (D), threonine (T), glutamic acid (E), serine (S), cysteine (C), alanine (A), glycine (G), or valine (V).

2) Substitutions suitable for improvement of activity under neutral condition 2-1) Amino acid residues after substitution at position 136 (under neutral condition)

(i') Enhancement of activity for L-leucine (under neutral condition)

Alanine (A), cysteine (C), phenylalanine (F), glycine (G), histidine (H), lysine (K), leucine (L), methionine (M), asparagine (N), arginine (R), serine (S), tryptophan (W), or tyrosine (Y).

(ii') Enhancement of activity for L-isoleucine (under neutral condition)

Alanine (A), cysteine (C), phenylalanine (F), glycine (G), histidine (H), lysine (K), leucine (L), methionine (M), asparagine (N), arginine (R), serine (S), tryptophan (W), or tyrosine (Y).

(iii') Enhancement of activity for L-valine (under neutral condition)

Alanine (A), cysteine (C), phenylalanine (F), glycine (G), histidine (H), lysine (K), leucine (L), methionine (M), asparagine (N), glutamine (Q), arginine (R), serine (S), tryptophan (W), or tyrosine (Y).

2-2) Amino acid residues after substitution at position 292 (under neutral condition)

(iv') Enhancement of activity for L-leucine (under neutral condition)

Alanine (A), cysteine (C), aspartic acid (D), glutamic acid (E), phenylalanine (F), glycine (G), histidine (H), lysine (K), leucine (L), methionine (M), asparagine (N), glutamine (Q), arginine (R), serine (S), threonine (T), valine (V), tryptophan (W), or tyrosine (Y).

(v') Enhancement of activity for L-isoleucine (under neutral condition)

Alanine (A), cysteine (C), aspartic acid (D), glutamic acid (E), phenylalanine (F), glycine (G), histidine (H), lysine (K), leucine (L), methionine (M), asparagine (N), glutamine (Q), arginine (R), serine (S), threonine (T), tryptophan (W), or tyrosine (Y).

(vi') Enhancement of activity for L-valine (under neutral condition)

Alanine (A), cysteine (C), aspartic acid (D), glutamic acid (E), phenylalanine (F), glycine (G), histidine (H), lysine (K), leucine (L), methionine (M), asparagine (N), glutamine (Q), arginine (R), serine (S), threonine (T), valine (V), tryptophan (W), or tyrosine (Y).

In still another embodiment, the thermal stability of the leucine dehydrogenase is improved as the property of the leucine dehydrogenase which is associated with the measurement of the total branched-chain amino acids. The improvement of the thermal stability of the leucine dehydrogenase means that the thermal stability of the modified enzyme is further enhanced relative to that of the wild-type enzyme. Specifically, the improvement of the thermal stability of the leucine dehydrogenase can be accomplished when a remaining activity of the modified enzyme is higher than that of the wild-type enzyme when the enzyme is treated in an aqueous solution at 60° C. for one hour. A thermal stability test of the leucine dehydrogenase in the aqueous solution can have significance as an acceleration test for evaluating the stability (particularly liquid stability) of the leucine dehydrogenase. Therefore, when the thermal stability of the modified enzyme in the aqueous solution is high, the stability (particularly liquid stability) of the modified enzyme also tends to be high. An enzyme showing high liquid stability can be stored in a liquid form for a long period of time, and thus, such a modified enzyme is useful as a liquid reagent for the measurement of the total branched-chain amino acids. A level of the enhancement of the thermal stability of the modified enzyme can be 1.1 fold or more or 1.2 fold or more relative to that of the wild-type enzyme. Examples of the modification in the modified enzyme of the present invention having 1.1 fold or more enhanced thermal stability relative to the wild-type enzyme may include the substitution of isoleucine (I) in the TGI motif with the following amino acid residue and/or the substitution of isoleucine (I) in the GVI motif with the following amino acid residue.

Amino acid residues after substitution at position 136

Methionine (M), arginine (R), phenylalanine (F), or lysine (K).

Amino acid residues after substitution at position 292

Phenylalanine (F)

The modified enzyme of the present invention may also have another peptide component (e.g., a tag moiety) at the C-terminus or N-terminus. Examples of the other peptide component that can be added to the modified enzyme of the present invention may include peptide components that make purification of the objective protein easy (e.g., tag moiety such as histidine tag and strep-tag II; proteins such as glutathione-S-transferase and maltose-binding protein commonly used for the purification of the objective protein), peptide components that enhance solubility of the objective protein (e.g., Nus-tag), peptide components that work as a chaperon (e.g., trigger factor), and peptide components as a protein or a domain of the protein having another function or a linker connecting them.

The modified enzyme of the present invention may also have supplemental mutations (e.g., substitutions, deletions, insertions and additions) of one or several amino acid residues in an amino acid sequence of the leucine dehydrogenase having the above mutation(s) as long as the aforementioned property is retained. The number of amino acid residues in which the supplemental mutation can be introduced are, for example, 1 to 100, 1 to 50, 1 to 40, 1 to 30 or even 1 to 20 or 1 to 10 (e.g., 1, 2, 3, 4 or 5). A person skilled in the art can appropriately make such a modified enzyme retaining the aforementioned property.

Therefore, the modified enzyme of the present invention may be the following (i) or (ii):

a protein having an amino acid sequence having a mutation or mutations (e.g., substitution) of isoleucine (I) in the TGI motif and/or isoleucine (I) in the GVI motif in an amino acid sequence of the leucine dehydrogenase, and having the improved property of the leucine dehydrogenase which is associated with the measurement of total branched-chain amino acids; or a protein having an amino acid sequence having a supplemental mutation of one or several amino acid residues in the amino acid sequence having a mutation or mutations (e.g., substitution) of isoleucine (I) in the TGI motif and/or isoleucine (I) in the GVI motif in the amino acid sequence of the leucine dehydrogenase, and having the improved property of the leucine dehydrogenase which is associated with the measurement of the total branched-chain amino acids.

The modified enzyme of the present invention may also be that having an amino acid sequence having at least 90% or more sequence identity to the amino acid sequence of the (wild-type) leucine dehydrogenase before its mutation because of having both the aforementioned mutation or mutations and the supplemental mutation or mutations. A percentage of the amino acid sequence identity may be 92% or more, 95% or more, 97% or more, or 98% or more or 99% or more.

The identity between the amino acid sequences can be determined, for example, using algorithm BLAST by Karlin and Altschul (Pro. Natl. Acad. Sci. USA, 90, 5873 (1993)) and FASTA by Pearson (MethodsEnzymol., 183, 63 (1990)). A program referred to as BLASTP has been developed based on this algorithm BLAST (see http://www.ncbi.nlm.nih.gov). Thus, the identity between the amino acid sequences may be calculated using these programs with the default setting. Also, for example, a numerical value obtained by calculating similarity as a percentage using a full length polypeptide portion encoded in an ORF and using software GENETYX Ver. 7.09 with setting of Unit Size to Compare=2 from Genetyx Corporation employing Lipman-Pearson method may be used as the identity between the amino acid sequences. The lowest value among the values derived from these calculations may be employed as the identity between the amino acid sequences.

The position of an amino acid residue at which the supplemental mutation can be introduced in an amino acid sequence would be apparent to a person skilled in the art. For example, the supplemental mutation can be introduced with reference to an alignment of the amino acid sequence. Specifically, a person skilled in the art can (1) compare amino acid sequences of a plurality of homologs (e.g., an amino acid sequence represented by SEQ ID NO:2 and an amino acid sequence of the other homolog(s)), (2) demonstrate relatively conserved regions and relatively not conserved regions, then (3) predict regions capable of playing a functionally important role and regions incapable of playing a functionally important role from the relatively conserved regions and the relatively not conserved regions, respectively, and thus recognize correlativity between a structure and a function. The analysis result of the three-dimensional structure has been reported for leucine dehydrogenases as described above. Thus, a person skilled in the art can introduce the supplemental mutation based on the analysis result of the three-dimensional structure so as to enable the retention of the aforementioned property.

When the supplemental mutation of the amino acid residue is a substitution, such a substitution of the amino acid residue may be a conservative substitution. The term "conservative substitution" refers to substituting a given amino acid residue with an amino acid residue having a similar side chain. Families of the amino acid residues having the similar side chain are well-known in the art. Examples of such families may include amino acids having a basic side chain (e.g., lysine, arginine, histidine), amino acids having an acidic side chain (e.g., aspartic acid, glutamic acid), amino acids having an uncharged polar side chain (e.g., asparagine, glutamine, serine, threonine, tyrosine, cysteine), amino acids having a nonpolar side chain (e.g., glycine, alanine, valine, leucine, isoleucine, proline, phenylalanine, methionine, tryptophan), amino acids having a branched side chain at position β (e.g., threonine, valine, isoleucine), amino acids having an aromatic side chain (e.g., tyrosine, phenylalanine, tryptophan, histidine), amino acids having a side chain containing a hydroxyl (e.g., alcoholic, phenolic) group (e.g., serine, threonine, tyrosine), and amino acids having a sulfur-containing side chain (e.g., cysteine, methionine). For example, the conservative substitution of the amino acid may be the substitution between aspartic acid and glutamic acid, the substitution between arginine, lysine and histidine, the substitution between tryptophan and phenylalanine, the substitution between phenylalanine and valine, the substitution between leucine, isoleucine and alanine, and the substitution between glycine and alanine.

The modified enzyme of the present invention can be prepared using a transformant of the present invention, which expresses the modified enzyme of the present invention or a cell-free system. The transformant of the present invention can be made, for example, by making an expression vector for the modified enzyme of the present invention and introducing this expression vector into a host. For example, the transformant of the present invention can be obtained by making the expression vector in which the polynucleotide of the present invention has been incorporated and introducing this vector into an appropriate host. Various prokaryotic cells including cells from bacteria belonging to genera *Escherichia* (e.g., *Escherichia coli*), *Corynebacterium* (e.g., *Corynebacterium glutamicum*) and *Bacillus* (e.g., *Bacillus subtilis*), and various eukaryotic cells including cells from fungi belonging to genera *Saccharomyces* (e.g., *Saccharomyces cerevisiae*), *Pichia* (e.g., *Pichia stipitis*) and *Aspergillus* (e.g., *Aspergillus oryzae*) can be used as the host for expressing the modified enzyme of the present invention. A strain in which a certain gene has been deleted may be used as the host. Examples of the transformant may include transformants in which the vector is retained in its cytoplasm and transformants in which an objective gene is integrated into its genome.

The transformant of the present invention can be cultured in a medium having a composition described later using a given culture apparatus (e.g., test tube, flask, jar fermenter). A culture condition can appropriately be determined. Specifically, a culture temperature may be 25 to 37° C., a pH value may be 6.5 to 7.5, and a culture period may be 1 to 100 hours. Cultivation may also be carried out by managing the dissolved oxygen concentration. In this case, the dissolved oxygen concentration (DO value) may be used as an indicator for control. A ventilation/stirring condition can be controlled so that the relative dissolved oxygen concentration, the DO value, does not fall below 1 to 10% for example, or not below 3 to 8% when an oxygen concentration in the air is 21%. The cultivation may be a batch cultivation or a fed-batch cultivation. In the case of the fed-batch cultivation, the cultivation can also be continued by sequentially adding continuously or discontinuously a solution as a sugar source and a solution containing phosphoric acid to the culture medium.

The host to be transformed is as described above, and can be *Escherichia coli*, or the host can be *Escherichia coli* K12 subspecies *Escherichia coli* JM109 strain, DH5α strain, HB101 strain, BL21 (DE3) strain, and the like. Methods of performing the transformation and methods of selecting the transformant have been described in Molecular Cloning: A Laboratory Manual, 3rd edition, Cold Spring Harbor press (Jan. 15, 2001), and the like. Hereinafter, a method of making transformed *Escherichia coli* and producing a predetermined enzyme using this will be described specifically by way of example only.

A promoter used for producing a foreign protein in *E. coli* can generally be used as a promoter for expressing the polynucleotide of the present invention. Examples thereof may include potent promoters such as a PhoA, PhoC, T7 promoter, a lac promoter, a trp promoter, a trc promoter, a tac promoter, PR and PL promoters of lambda phage, and a T5 promoter, and the PhoA, PhoC and lac promoters are preferred. For example, pUC (e.g., pUC19, pUC18), pSTV, pBR (e.g., pBR322), pHSG (e.g., pHSG299, pHSG298, pHSG399, pHSG398), RSF (e.g., RSF1010), pACYC (e.g., pACYC177, pACYC184), pMW (e.g., pMW119, pMW118, pMW219, pMW218), pQE (e.g., pQE30) and derivatives thereof may be used as a vector. A vector from phage DNA may also be utilized as the other vector. Further, an expression vector that includes a promoter and can express an inserted DNA sequence may also be used. Preferably, the vector may be pUC, pSTV, or pMW.

Also, a terminator that is a transcription terminating sequence may be ligated downstream of the polynucleotide of the present invention. Examples of such a terminator may include a T7 terminator, an fd phage terminator, a T4 terminator, a terminator of a tetracycline resistant gene, and a terminator of *Escherichia coli* trpA gene.

The vector for introducing the polynucleotide of the present invention into *Escherichia coli* can be a so-called multicopy type, and examples thereof may include plasmids which have an replication origin from ColE1, such as pUC-based plasmids, pBR322-based plasmids and derivatives thereof. Here the "derivative" means those in which the modification has been given to the plasmid by substitution, deletion, insertion and/or addition of base(s). The "modification" referred to herein also includes modification by mutagenesis using a mutating agent, UV irradiation or the like, or naturally occurring mutations.

In order to select the transformant, the vector can have a marker such as an ampicillin resistant gene. Expression vectors having a potent promoter are commercially available as such a plasmid (e.g., pUC-based (supplied from Takara Bio Inc.), pPROK-based (supplied from Clontech), pKK233-2-based (supplied from Clontech)).

The modified enzyme of the present invention can be obtained by transforming *Escherichia coli* using the resulting expression vector of the present invention and culturing this *Escherichia coli.*

Media such as M9/casamino acid medium and LB medium generally used for culturing *Escherichia coli* may be used as the medium. The medium may contain a predetermined carbon source, nitrogen source, and coenzyme (e.g., pyridoxine hydrochloride). Specifically, peptone, yeast extract, NaCl, glucose, $MgSO_4$, ammonium sulfate, potassium dihydrogen phosphate, ferric sulfate, manganese sulfate, and the like may be used. A cultivation condition and a production inducing condition are appropriately selected depending on types of a marker and a promoter in a vector and a host to be used.

The modified enzyme of the present invention can be recovered by the following methods. The modified enzyme of the present invention can be obtained as a pulverized or lysed product by collecting the transformant of the present invention and subsequently pulverizing (e.g., sonication or homogenization) or lysing (e.g., treatment with lysozyme) the microbial cells. The modified enzyme of the present invention can be obtained by subjecting such a pulverized or lysed product to techniques such as extraction, precipitation, filtration, and column chromatography.

The present invention also provides a method of analyzing the total branched-chain amino acids. The analysis method of the present invention can include the steps of measuring the total branched-chain amino acids contained in a test sample using the modified enzyme of the present invention.

The test sample is not particularly limited as long as the sample is suspected of containing any branched-chain amino acid (preferably the total branched-chain amino acids), and examples thereof may include biological samples (e.g., blood, urine, saliva, tear, and the like) and food and beverage (e.g., nutrient drinks and amino acid beverages).

The analysis method of the present invention is not particularly limited as long as the total branched-chain amino acids can be measured using the modified enzyme of the present invention. For example, the total branched-chain amino acids can be measured by mixing the test sample with nicotinamide adenine dinucleotide ($NAD^+$) under the alkaline condition or the neutral condition, preferably in alkaline buffer, then subjecting the mixed sample to an enzymatic reaction using the modified enzyme of the present invention, and finally detecting NADH formed from $NAD^+$ by the action of the modified enzyme of the present invention. Specifically, by allowing the modified enzyme to act upon the test sample in the alkaline buffer in the presence of nicotinamide adenine dinucleotide ($NAD^+$), the reduced form (NADH) is generated from nicotinamide adenine dinucleotide ($NAD^+$) while an amino group of a substrate contained in the biological sample is oxidatively deaminated. Thus, the total branched-chain amino acids can be quantified by detecting NADH by an absorbance (340 nm) or the like. The methods of measuring the amino acid by such a methodology are known (see e.g., Ueatrongchit T, Asano Y, Anal Biochem., 2011 Mar. 1; 410(1): 44-56). The total branched-chain amino acids can also be quantified by reducing a dye with the formed NADH and detecting color development of the reduced dye as an absorbance or the like. Further, NADH can also be detected by an electrochemical technique. For example, it is possible to measure the total branched-chain amino acids by electrochemically oxidizing NADH formed by allowing the modified enzyme to act upon the test sample under the alkaline or neutral condition and measuring its oxidation electric current, or by reducing a coexisting electronic mediator by the formed NADH and measuring oxidation electric current when the reduced electronic mediator is electrochemically oxidized. An electronic transfer between the NADH and the electronic mediator may be mediated by a catalyst. The total branched-chain amino acids can be measured by the rating method (initial rate method).

The modified enzyme of the present invention is not reacted with amino acids other than the branched-chain amino acids or has a low reactivity therewith. Therefore, even when not only the branched-chain amino acids but also other amino acids are contained in a test sample, an amount of the branched-chain amino acids in the test sample can be evaluated by using the modified enzyme of the present invention.

Further, the present invention includes a kit for analyzing the total branched-chain amino acids including the modified enzyme of the present invention.

The kit of the present invention can further include at least one of a buffer solution or a buffer salt for a reaction and nicotinamide adenine dinucleotide ($NAD^+$).

The buffer solution or the buffer salt for the reaction is used for keeping a pH value in a reaction solution suitable for an objective enzymatic reaction. The buffer solution or the buffer salt for the reaction is alkaline or neutral, and preferably alkaline.

When the kit of the present invention includes nicotinamide adenine dinucleotide ($NAD^+$), the kit of the present invention may further include a dye to be reduced by NADH. In this case, the dye is reduced by NADH formed from $NAD^+$ by an action of the modified enzyme of the present invention, and the color development from the reduced dye can be detected by the absorbance and the like. A substance working as an electronic mediator may be involved in the reduction of the dye.

The present invention also provides an enzyme sensor for analyzing the branched-chain amino acid including (a) an electrode for detection and (b) the modified enzyme of the present invention immobilized or retained on the electrode for detection. The modified enzyme of the present invention is immobilized or retained on the electrode directly or indirectly.

It is possible to use, for example, a biosensor that directly or indirectly detects a product or a byproduct ($NH_3$+NADH+$H^+$) formed form the total branched-chain amino acids by the modified enzyme of the present invention as the electrode for detection. More specifically, examples of the electrode for detection include an electrode for detection utilizing the modified enzyme of the present invention and nicotinamide adenine dinucleotide ($NAD^+$). Those described in International Publication No. WO2005/075970 and International Publication No. WO00/57166 or others can be used as such an electrode for detection.

EXAMPLES

The present invention will be described in detail with reference to following Examples, but the present invention is not limited thereto.

Enzymatic Quantification Method

In an enzymatic quantification method for L-leucine, L-isoleucine and L-valine, leucine dehydrogenase was allowed to act upon a biological sample (e.g., plasma) in alkaline buffer in the presence of nicotinamide adenine dinucleotide ($NAD^+$), and an amino group in a substrate contained in the biological sample was oxidatively deaminated, as well as a reduced product (NADH) was formed from nicotinamide adenine dinucleotide ($NAD^+$). The amount of NADH that formed was measured using a microplate reader (SpectraMax M2e, supplied from Molecular Devices).

Example 1

Production of Modified Enzyme (I136R)

(1) Preparation of Template ldh Gene (a) Culture and Purification of Chromosomal DNA A lyophilized pellet of *Geobacillus stearothermophilus* NBRC 12550 obtained from National Institute of Technology and Evaluation, Biological Resource Center (NBRC) was suspended in a growth medium 702, which was then applied onto an agar medium of a growth medium 802 and cultured overnight at 50° C. A resulting colony was inoculated in 5 mL of the growth medium 702 and statically cultured at 50° C. for 30 hours. Chromosomal DNA was purified from 5 mL of this cell culture, and subjected to the following experiment.

Details for preparing the media are as described in Table 3.

TABLE 3

| Composition of media | |
|---|---|
| **Growth medium 702** | |
| Polypeptone | 10 g |
| Yeast extract | 2 g |
| $MgSO_4 \cdot 7H_2O$ | 1 g |
| Distilled water | 1 L (pH 7.0) |
| **Growth medium 802** | |
| Polypeptone | 10 g |
| Yeast extract | 2 g |
| $MgSO_4 \cdot 7H_2O$ | 1 g |
| Agar | 15 g |
| Distilled water | 1 L (pH 7.0) |

(b) Preparation of Plasmid pUC18His plasmid made by the method described in Biosci. Biotechnol. Biochem. 2009; 73: 729-732 was purified from a culture medium of recombinant *Escherichia coli* (*E. coli* JM109/pUC18His) carrying a vector using Invisorb Spin Plasmid Mini Kit (supplied from Invitek) according to manufacturer's protocol. Subsequently, 7 μL of vector DNA of purified plasmid pUC18His, 2.5 μL of 10×K buffer (supplied from Takara Bio Inc.) and each 0.8 μL of PstI and BamHI were mixed, sterilized ultrapure water was added to make a total volume of a reaction solution 25 μL, and then the mixture was treated with the restriction enzymes at 37° C. for 3 hours. Then, 2 μL of alkaline phosphatase derived from shrimp (supplied from Roche) and 5 μL of ×10 alkaline phosphatase buffer were added to 25 μL of the above reaction solution, and sterilized ultrapure water was added to make a total volume of a reaction solution 50 μL, and then the mixture was reacted at 37° C. for one hour. The reaction solution was purified by phenol/chloroform extraction and ethanol precipitation to obtain 20 μL of dephosphorylated pUC18His vector DNA dissolved in a TE solution.

(c) Amplification of Leucine Dehydrogenase Gene

*G. stearothermophilus* chromosomal DNA was used as a template, and a synthesized oligonucleotide primer 1: 5'-CCGGATCCGATGGAATTGT-TCAAATATATGGAAAC-3' (SEQ ID NO:11) (supplied from Hokkaido System Science Co., Ltd) containing a BamHI recognition site sequence and a synthesized oligonucleotide primer 2: 5'-ACTGCAGTTATATTGCCGAAG-CACC-3' (SEQ ID NO:12) (supplied from Hokkaido System Science Co., Ltd) containing a PstI recognition site sequence, which had been both made based on a leucine dehydrogenase gene from *G. stearothermophilus* IFO 12550 (SEQ ID NO: 1; Biochemistry, 27, 9056 (1988)) were used in amplification of the leucine dehydrogenase gene derived from *G. stearothermophilus*. As a PCR reaction solution, 50 ng of chromosomal DNA, each 1 μL of the synthesized nucleotide primers at 100 pmol/μL, 5 μL of ExTaq×10 buffer (supplied from Takara Bio Inc.), 5 μL of 2.5 mM dNTP mixture (supplied from Takara Bio Inc.), and 1 μL of TaKaRa ExTaq DNA polymerase (supplied from Takara Bio Inc.) were mixed, and sterilized ultrapure water was added to make a total volume of the reaction solution 50 μL. PCR was performed using PTC-200 Peltier thermal cycler (supplied from MJ Research Japan), and the reaction at 94° C. for 30 seconds, 55° C. for 30 seconds and 72° C. for 2 minutes was repeated in 30 cycles.

A PCR product was electrophoresed, and two amplified products (around 1400 bp and 1900 bp) cut out under ultraviolet irradiation was extracted and purified using a gel extraction kit Gel-M™ Gel Extraction Kit (supplied from VIOGENE) to obtain 50 μL of a purified product. Subsequently, 6 μL of 10×K buffer (supplied from Takara Bio Inc.) and each 1 μL of PstI and BamHI were added to 4 μL of the purified product, and sterilized ultrapure water was added to make a total volume of the reaction solution 60 μL. The reaction solution was reacted at 37° C. for 3 hours to treat both ends of the purified PCR product with the restriction enzymes. The reaction solution was incubated at 60° C. for 15 minutes to inactivate the restriction enzymes. Subsequently the ethanol precipitation was performed to obtain a purified insertion fragment.

(d) Ligation and Transformation

1 μL of the dephosphorylated plasmid obtained above, 5 μL of the purified insertion fragment, and 6 μL of Ligation Mix (supplied from Takara Bio Inc.) were mixed, a total volume of a reaction solution was made 12 μL, and a ligation reaction was performed at 16° C. overnight. Subsequently, *E. coli* JM109 was transformed with 6 μL of the reaction solution after the ligation reaction, applied onto an LB agar medium containing 50 μg/mL of ampicillin, and cultured at 37° C. for 10 hours. A resulting colony was inoculated to a master plate and cultured, and then a newly formed colony was inoculated to 5 mL of the LB agar medium containing 50 μg/mL of ampicillin and cultured overnight. Plasmid DNA was purified from the culture, and its nucleotide sequence was analyzed using ABI PRISM 310 Genetic Analyzer (supplied from Applied Biosystems). A clone confirmed to have the correct nucleotide sequence of the leucine dehydrogenase gene derived from *G. stearothermophilus* was designated as *E. coli* JM109/pUCHisLDH.

(2) Production of Modified Enzyme of Leucine Dehydrogenase Derived from *Geobacillus stearothermophilus*

An expression plasmid for a modified enzyme (I136R) was made by introducing a site-directed mutation into pUCHisLDH using QuikChange Lightning Site-Directed Mutagenesis Kits (Agilent Technologies) according to the protocol attached to the product. At that time, a sequence: 5'-GACTATGTCACCGGCCGTTCGCCCGAATTCGG-3' (SEQ ID NO:9) and a sequence: 5'-CCGAATTCGGGCGAACGGCCGGTGACATAGTC-3' (SEQ ID NO:10) were used as a sense primer containing a mutated codon and an antisense primer, respectively. Experimental manipulations associated with transformation, cultivation, plasmid extraction, and the like were carried out according to standard methods. A clone identified to have an objective nucleotide sequence was designated as *Escherichia coli* JM109/pUCHisLDH mutant and used for subsequent experiments.

(3) Expression and Purification of Modified Enzyme

Expression and purification of the modified enzyme constructed as described previously are shown below. A colony of recombinant *Escherichia coli* transformed with the plasmid pUCHisLDH mutant containing the gene encoding the modified enzyme (*Escherichia coli* JM109/pUCHisLDH mutant) was cultured with shaking in a test tube containing 5 mL of the LB medium containing 50 μg/mL of ampicillin salt at 37° C. for 16 hours. This culture was inoculated to a 0.5 liter Sakaguchi flask containing 100 mL of the LB medium containing 50 μg/mL of ampicillin salt, and cultured with shaking at 37° C. until O.D. reached 1.0. Then, 1 M isopropyl-β-D-galactoside (IPTG supplied from Nacalai Tesque Inc.) was added at a final concentration of 1 mM, and the cultivation with shaking was further continued for additional 5 hours. The resulting cultured medium was centrifuged (8,000 rpm, 15 minutes, 4° C.; Hitachi high speed cooled centrifuge, HIMAC CR21G supplied from Hitachi Ltd.) to precipitate cultured microbial cells, and a supernatant was discarded. The obtained microbial cells were suspended in 50 mM $NaH_2PO_4$ buffer (pH 8.0) containing 300 mM NaCl and 10 mM imidazole. Then, the microbial cells were disrupted and the enzyme was extracted using an ultrasonic disruption apparatus (KUBOTA INSONATOR model 201M, supplied from Kubota Corporation) at 180 W for 15 minutes at 4° C. A cell lysate was centrifuged (8,000 rpm, 15 minutes, 4° C.; Hitachi high speed cooled centrifuge, HIMAC CR21G supplied from Hitachi Ltd.) and a supernatant was used as a cell-free extract solution for the purification of an enzymatic protein. The cell-free extract solution was applied onto a column filled with 1 mL of Ni-NTA resin (supplied from Qiagen) and equilibrated with buffer (50 mM $NaH_2PO_4$ buffer (pH 8.0) containing 300 mM NaCl and 10 mM imidazole). The resin was washed with 5 mL of washing buffer (50 mM $NaH_2PO_4$ buffer (pH 6.5) containing 1 M NaCl and 20 mM imidazole), and subsequently a bound enzymatic protein was eluted with 5 mL of elution buffer (50 mM $NaH_2PO_4$ buffer (pH 8.0) containing 300 mM NaCl and 250 mM imidazole). The eluted fraction was concentrated using an ultrafiltration membrane (e.g., Vivaspin6 100 kDa MWCO supplied from GE Healthcare). A protein concentration was measured using Micro BCA Protein Assay Kit (supplied from Thermo Fisher Scientific) and calculated based on a standard curve prepared using predetermined concentration of bovine serum albumin. A purity of the purified enzyme was confirmed by sodium dodecyl sulfate/polyacrylamide gel electrophoresis. Subsequent experiments were carried out using the obtained purified enzyme.

Example 2

Evaluation of Substrate Specificity

Figure 2:
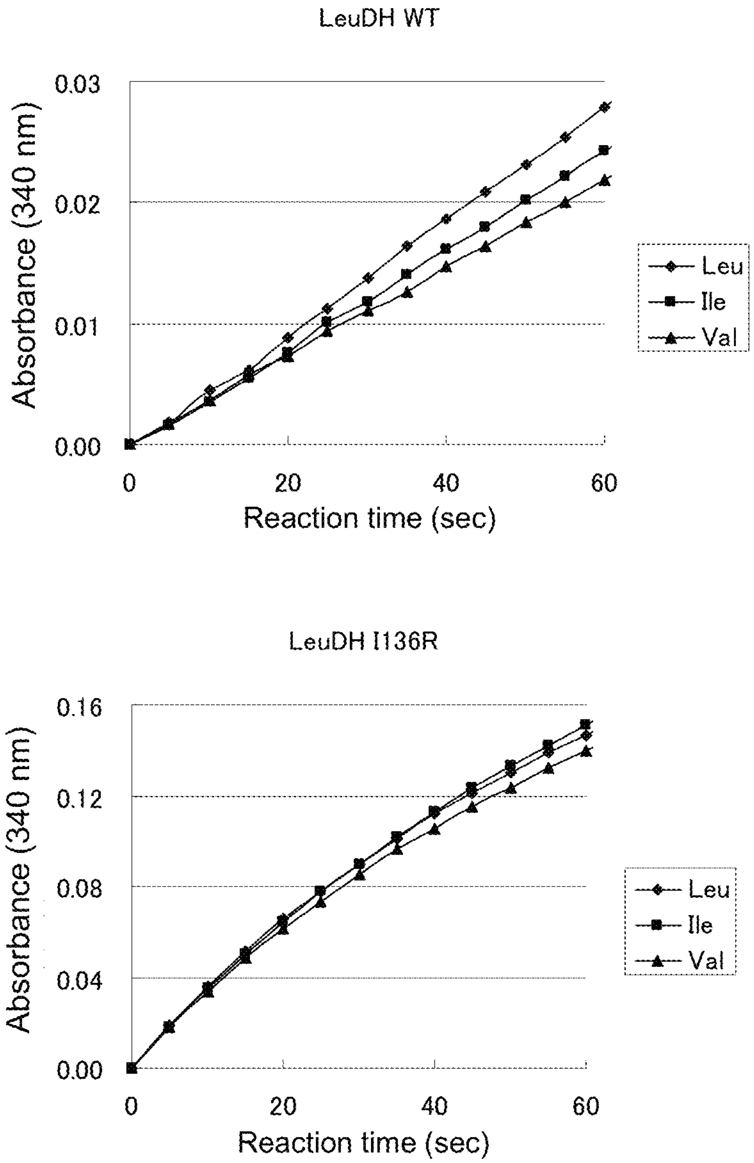
FIG. 2 shows changes of absorbance with time (means of n=3) when each branched-chain amino acid (L-leucine, L-isoleucine and L-valine) was reacted with a wild-type enzyme or the modified enzyme I136R.

An activity of leucine dehydrogenase was measured in a cuvette with 1 cm of an optical pass length (supplied from Bio-Rad) using a microplate reader also capable of using a cuvette (SpectraMax M2e, supplied from Molecular Devices) according to Asano et al.'s method (Eur. J. Biochem. (1987) 168 (1), 153-159). A composition of a reaction solution was as follows. 0.5 mL of 0.2 M Glycine-KCl—KOH buffer (pH9.0), 0.04 mL of a solution of 25 mM NAD (supplied from Sigma), and 0.1 mL of a solution of 0.1 M L-leucine (supplied from Sigma) or L-isoleucine (supplied from Sigma) or L-valine (supplied from Sigma) and an appropriate amount of an enzyme solution were added to make a total volume of the reaction solution 1.0 mL. An enzymatic reaction was performed at room temperature for one minute, and change of an absorbance at 340 nm was measured. The results are shown in FIG. 2. A relative activity of the modified enzyme (I136R) to which the mutation had been introduced using the wild-type (WT) as the template was improved for each BCAA. Hereinafter, the wild-type is sometimes abbreviated as WT.

Example 3

Preparation of Standard Curve for Reaction of BCAA with Modified Enzyme (I136R)

0.5 mL of 0.2 M Glycine-KCl—KOH buffer (pH9.0), 0.04 mL of a solution of 25 mM $NAD^+$ (supplied from Sigma), and a known concentration of an L-leucine or L-isoleucine or L-valine aqueous solution were mixed, and MilliQ water was added to make a total volume of 0.96 mL. This mixture was added to a cuvette. To this solution, 0.04 mL of 0.5 mg/mL enzyme solution was added to make a total volume of 1 mL, and the resulting solution was mixed upside down. The enzymatic reaction was performed at room temperature for one minute, and the change of the absorbance at 340 nm was measured.

Figure 3:
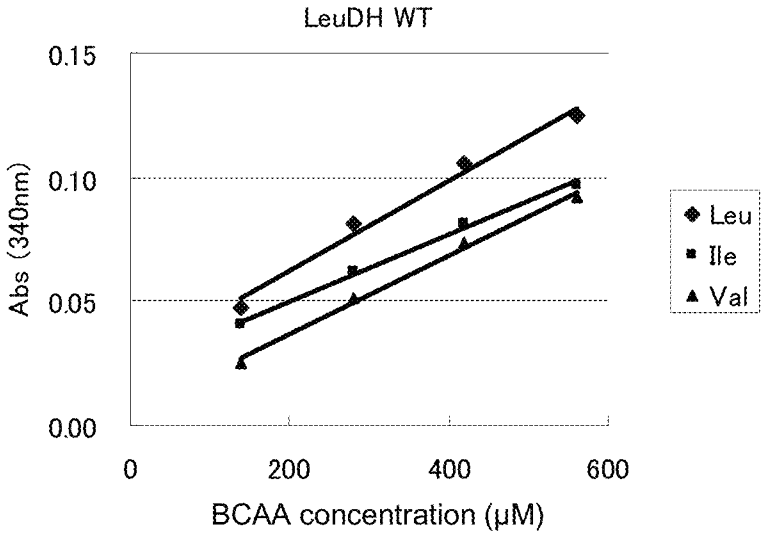
FIG. 3 shows activities of the wild-type enzyme or the modified enzyme I136R for each branched-chain amino acid (L-leucine, L-isoleucine and L-valine) at various concentration as changes of absorbance (means of n=3) and showing standard curves prepared from those values.
Figure 3:
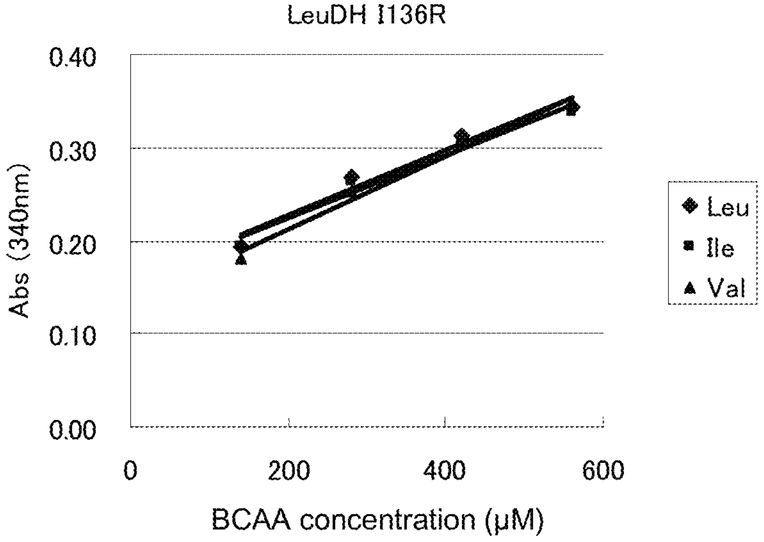

The results of the above measurement are shown in FIG. 3. When BCAA concentrations were 140 to 560 μM (measured at 4 points of 140, 280, 420 and 560 μM), the standard curves for Leu, Ile and Val were largely different in the case of WT because the activity of WT for each BCAA was different. On the other hand, the standard curves for the reaction of Leu, Ile and Val with the modified enzyme I136R were almost the same because its activity for each BCAA was almost the same. From the above, it was revealed that according to the modified enzyme I136R, the total BCAA concentration in even a sample containing any two or all of Leu, Ile and Val in mixture could be considered as concentration of any one of Leu, Ile and Val.

Example 4

Quantification of Total BCAA in Actual Sample by Modified Enzyme I136R

Rat plasma samples (SD strain, females, 20 weeks of age, supplied from Charles River Laboratories Japan, Inc.) were used as actual samples, and total BCAA in the sample was measured by LeuDH WT and LeuDH I136R. The measurement was evaluated by comparing total BCAA measurement values calculated by the enzymatic method with total BCAA measurement values obtained by an amino acid analyzer L-8900 (supplied from Hitachi High Technologies Corporation).

The quantification of total BCAA by the enzymatic method was carried out according to the following procedure. 0.5 mL of 0.2 M Glycine-KCl—KOH buffer (pH9.0), 0.04 mL of a solution of 25 mM $NAD^+$ (supplied from Sigma), and 0.04 mL or 0.02 mL of a known concentration of an L-valine aqueous solution or a rat plasma sample were mixed, and MilliQ water was added to make a total volume of 0.96 mL. This mixture was added to a cuvette. To this solution, 0.04 mL of 0.5 mg/mL enzyme solution was added to make a total volume of 1 mL, and the resulting solution was mixed upside down. The enzymatic reaction was performed at room temperature for one minute, and the change of the absorbance at 340 nm was measured. The total BCAA in the plasma sample was quantified using a standard curve made by using the L-valine aqueous solution.

Deproteinization by sulfosalicylic acid was performed in the rat plasma samples for measuring by the amino acid analyzer.

Figure 4:
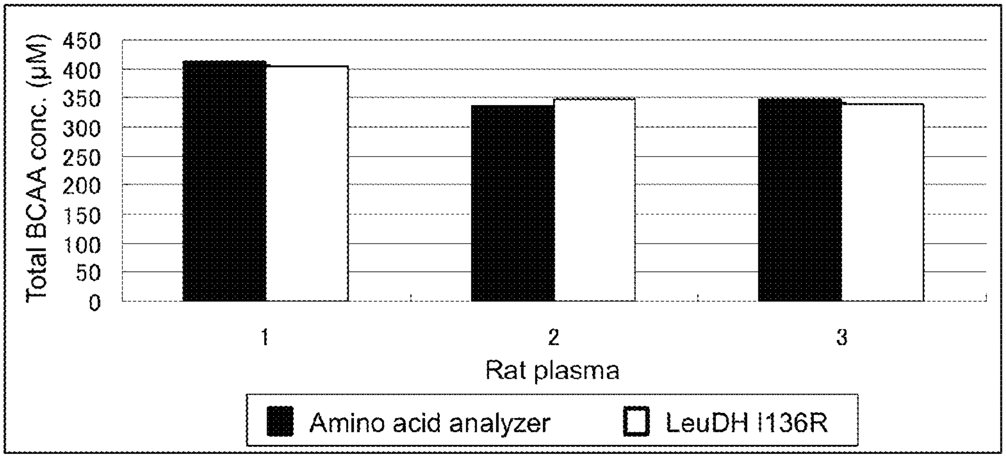
FIG. 4 shows concentrations of total BCAA (means of n=3) in plasma samples from rats measured by an enzymatic method and an amino acid analyzer.

A graph comparing respective measurement values of the total BCAA concentration in the rat plasma samples obtained by the enzymatic method and by the amino acid analyzer is shown in FIG. 4. As a result, the measurement values of the total BCAA concentration in the actual samples obtained by the enzymatic method were almost the same as the measurement values of the total BCAA obtained by the amino acid analyzer. The wild-type leucine dehydrogenase is known to scarcely have a catalytic activity for amino acids other than the branched-chain amino acids. The BCAA in the plasma sample containing a plurality of amino acids could be quantified in this experiment. Thus, the modified enzyme of the present invention is predicted to retain the property of the wild-type enzyme that the wild-type enzyme scarcely has the catalytic activity for the amino acids other than the branched chain amino acids. As described above, it was demonstrated that the modified enzyme of the present invention was useful for the measurement specific for the total BCAA in the actual sample.

Example 5

Synthesis of Modified Enzyme Using Cell-Free System and Purification of Modified Enzyme A histidine affinity tag and a TEV protease recognition site were fused to an N terminal side by a 2-step PCR method using a wild-type gene or an objective mutant gene as a template to prepare linear DNA of a construct having an introduced objective mutation. A protein was synthesized in a cell-free synthesis reaction system derived from *Escherichia coli* using this DNA as the template. A supernatant fraction after centrifugation of a product synthesized by a dialysis method for 6 hours using 1 mL of a reaction scale was purified with affinity for Ni to yield an elution fraction. Subsequently, the presence of a protein conceivable to be an objective enzyme was identified by SDS-PAGE and staining using SYPRO ORANGE protein gel stain (Life Technologies Japan Ltd.). A protein concentration in the yielded elution fraction was quantified by the Bradford method using BSA as a standard substance. The elution fraction was adjusted to an objective concentration as needed, and subsequently subjected to the evaluation. For the wild-type enzyme, the preparation of linear DNA, the cell-free synthesis, and the purification and analysis of the enzyme were performed in the same manner as above. Enzymes prepared by PCR using the wild-type gene as the template are shown in Table 4. Enzymes prepared by PCR using the gene carrying the introduced objective mutation as the template are shown in Tables 5 and 6. The resin and the buffer used for the purification are as follows.

Resin: Ni Sepharose High Performance (GE Healthcare Japan)

Buffer: Binding Buffer (NaCl 750 mM, NaPi 20 mM, pH8.0),

Wash Buffer (NaCl 750 mM, NaPi 20 mM, pH8.0)

Collection and measurement Buffer (NaCl 300 mM, NaPi 50 mM, EDTA 34 mM, pH7.0, 10% $D_2O$, 0.01% $NaN_3$)

Example 6

Evaluation of Activity and Substrate Specificity

The activity and the relative activity of the wild-type enzyme and the modified enzyme synthesized in Example 5 were evaluated according to the method in Example 2. The results are shown in Tables 4, 5 and 6. Mean values of results from 3 samples of the wild-type were used for values from WT in Tables 4 and 5. The results in Table 6 were calculated from mean values when the experiment was performed three times for the same sample. When the modified enzyme having a plurality of introduced mutations is represented, each of the introduced mutations was marked off using a slash and described consecutively. For example, a mutant I136R/I292F denotes a modified enzyme having two mutations of I136R and I292F. By introducing the mutation, the activity of the modified enzyme was further enhanced and/or became more equivalent for each BCAA, compared to that of WT. Compared to the case of introducing one mutation, the relative value of the activity for each BCAA became more equivalent by introducing two mutations that made the relative value more equivalent than WT.

TABLE 4

Relative values of activity of modified enzymes relative to WT (left) and relative values of activity of enzymes for each BCAA (right)(1).

| | Activity (change of absorbance per one minute) | | | | Relative activity (when activity for Leu is regarded as 100%) | | |
|---|---|---|---|---|---|---|---|
| | Leu | Ile | Val | | Leu | Ile | Val |
| I136C | 258% | 242% | 318% | I136C | 100% | 80% | 86% |
| I136Y | 204% | 218% | 241% | I136Y | 100% | 91% | 83% |
| I136A | 188% | 183% | 221% | I136A | 100% | 82% | 82% |
| I136G | 162% | 157% | 220% | I136G | 100% | 82% | 95% |
| I136S | 148% | 150% | 172% | I136S | 100% | 86% | 81% |
| I136N | 142% | 137% | 153% | I136N | 100% | 82% | 76% |
| I136W | 137% | 152% | 152% | I136W | 100% | 94% | 78% |
| I1360 | 108% | 113% | 113% | I1360 | 100% | 88% | 73% |
| I136E | 97% | 82% | 92% | I136E | 100% | 71% | 66% |
| I1361 | 95% | 95% | 93% | I1361 | 100% | 85% | 69% |
| I136P | 92% | 70% | 96% | I136P | 100% | 65% | 73% |
| I136D | 55% | 50% | 55% | I136D | 100% | 76% | 69% |
| I292H | 245% | 270% | 307% | I292H | 100% | 93% | 88% |
| I292N | 241% | 274% | 304% | I292N | 100% | 96% | 88% |
| I292Y | 234% | 265% | 274% | I292Y | 100% | 96% | 82% |
| I292L | 231% | 218% | 244% | I292L | 100% | 80% | 74% |
| I292K | 231% | 248% | 264% | I292K | 100% | 91% | 80% |
| I2920 | 223% | 250% | 262% | I2920 | 100% | 95% | 82% |
| I292R | 211% | 213% | 229% | I292R | 100% | 86% | 76% |
| I292D | 208% | 186% | 242% | I292D | 100% | 76% | 81% |
| I2921 | 202% | 218% | 226% | I2921 | 100% | 91% | 78% |
| I292E | 200% | 195% | 233% | I292E | 100% | 83% | 82% |

TABLE 4-continued

Relative values of activity of modified enzymes relative to WT (left) and relative values of activity of enzymes for each BCAA (right)(1).

| | Activity (change of absorbance per one minute) | | | | Relative activity (when activity for Leu is regarded as 100%) | | |
|---|---|---|---|---|---|---|---|
| | Leu | Ile | Val | | Leu | Ile | Val |
| I292S | 195% | 213% | 219% | I292S | 100% | 93% | 78% |
| I292C | 161% | 165% | 154% | I292C | 100% | 87% | 67% |
| I292A | 157% | 170% | 175% | I292A | 100% | 92% | 78% |
| I292G | 145% | 158% | 171% | I292G | 100% | 92% | 82% |

TABLE 4-continued

Relative values of activity of modified enzymes relative to WT (left) and relative values of activity of enzymes for each BCAA (right)(1).

| | Activity (change of absorbance per one minute) | | | | Relative activity (when activity for Leu is regarded as 100%) | | |
|---|---|---|---|---|---|---|---|
| | Leu | Ile | Val | | Leu | Ile | Val |
| I292V | 128% | 134% | 133% | I292V | 100% | 89% | 73% |
| I292W | 120% | 138% | 117% | I292W | 100% | 97% | 68% |
| I292P | 73% | 63% | 75% | I292P | 100% | 73% | 72% |
| WT | 100% | 100% | 100% | WT | 100% | 85% | 70% |

TABLE 5

Relative values of activity of modified enzymes relative to WT (left) and relative values of activity of enzymes for each BCAA (right)(2).

| | Activity (change of absorbance per one minute) | | | | Relative activity (when activity for Leu is regarded as 100%) | | |
|---|---|---|---|---|---|---|---|
| | Leu | Ile | Val | | Leu | Ile | Val |
| I136M | 250% | 300% | 370% | I136M | 100% | 93% | 102% |
| I136R | 239% | 279% | 330% | I136R | 100% | 91% | 95% |
| I136H | 191% | 206% | 180% | I136H | 100% | 83% | 65% |
| I136F | 184% | 238% | 277% | I136F | 100% | 100% | 102% |
| I136L | 180% | 171% | 240% | I136L | 100% | 73% | 92% |
| I136K | 150% | 171% | 217% | I136K | 100% | 88% | 99% |
| II36V | 75% | 65% | 63% | II36V | 100% | 66% | 57% |
| I292F | 268% | 362% | 370% | I292F | 100% | 105% | 95% |
| WT | 100% | 100% | 100% | WT | 100% | 76% | 66% |

TABLE 6

Relative values of activity of modified enzymes relative to WT (left) and relative values of activity of enzymes for each BCAA (right)(3).

| | Activity (change of absorbance per one minute) | | | | Relative activity (when activity for Leu is regarded as 100%) | | |
|---|---|---|---|---|---|---|---|
| | Leu | Ile | Val | | Leu | Ile | Val |
| I136R/I292F | 158% | 214% | 232% | I136R/I292F | 100% | 101% | 94% |
| WT | 100% | 100% | 100% | WT | 100% | 75% | 64% |

A 96-well microwell plate was used in place of the cuvette having 1 cm of the optical pass length, an enzymatic reaction was performed in the following reaction solution at 30° C. for one minutes, and then the change of the absorbance at 340 nm was measured. An enzyme to be used was synthesized using the linear DNA prepared using the wild-type gene as the template and purified as shown in Example 5. The reaction solution was prepared by mixing 150 μL of buffer (0.2 M HEPES, 0.28 M sodium chloride, 8.4 mM disodium hydrogen phosphate, pH 7.0 or 7.5 or 8.0), 30 μL of an aqueous solution of 25 mM $NAD^+$, 1.5 μL of an aqueous solution of 1 M potassium chloride, 3 μL of an aqueous solution of 10 mM L-leucine or L-isoleucine or L-valine and 100.5 μL of MilliQ water, and further adding 15 μL of 1 mg/mL of an enzyme solution thereto. The results are shown in Tables 7 and 8. Each value for I136K and I136R was obtained from one experiment, and other values for other enzymes were mean values calculated from two experiments for the same sample. Table 7 shows relative values of the activity of the modified enzymes relative to WT, and Table 8 shows relative values of activity of the enzymes for each BCAA.

TABLE 7

Relative values of activity of modified enzymes relative to WT.

| | Activity (change of absorbance per one minute) | | | | | | | | |
|---|---|---|---|---|---|---|---|---|---|
| | pH 7.0 | | | pH 7.5 | | | pH 8.0 | | |
| | Leu | Ile | Val | Leu | Ile | Val | Leu | Ile | Val |
| I136A | 258% | 182% | 412% | 174% | 164% | 234% | 143% | 176% | 210% |
| I136C | 328% | 233% | 610% | 206% | 206% | 314% | 157% | 218% | 285% |
| I136E | 69% | 47% | 66% | 40% | 35% | 30% | 27% | 25% | 17% |
| I136F | 252% | 270% | 538% | 152% | 208% | 255% | 136% | 194% | 214% |
| I136G | 270% | 207% | 488% | 188% | 188% | 255% | 153% | 201% | 219% |
| I136H | 292% | 251% | 375% | 191% | 223% | 211% | 157% | 199% | 186% |
| I136K | 231% | 219% | 436% | 170% | 200% | 236% | 152% | 188% | 203% |
| I136L | 291% | 236% | 497% | 185% | 219% | 271% | 158% | 196% | 227% |
| I136M | 317% | 255% | 588% | 179% | 240% | 327% | 153% | 226% | 277% |
| I136N | 235% | 199% | 301% | 187% | 171% | 176% | 150% | 167% | 139% |
| I136Q | 84% | 112% | 175% | 89% | 96% | 75% | 81% | 99% | 68% |
| I136R | 283% | 271% | 579% | 167% | 235% | 294% | 145% | 217% | 245% |
| I136S | 166% | 165% | 274% | 148% | 151% | 143% | 130% | 154% | 123% |
| I136T | 64% | 68% | 77% | 71% | 65% | 57% | 69% | 70% | 56% |
| I136V | 76% | 69% | 99% | 73% | 66% | 64% | 81% | 75% | 68% |
| I136W | 195% | 169% | 221% | 146% | 146% | 134% | 119% | 133% | 110% |
| I136Y | 257% | 236% | 522% | 158% | 193% | 244% | 134% | 178% | 201% |
| I292A | 208% | 176% | 309% | 160% | 185% | 180% | 132% | 162% | 178% |
| I292C | 224% | 135% | 335% | 177% | 184% | 199% | 146% | 168% | 164% |
| I292D | 396% | 339% | 739% | 236% | 278% | 359% | 183% | 253% | 277% |
| I292E | 335% | 381% | 666% | 216% | 325% | 359% | 162% | 267% | 287% |
| I292F | 396% | 532% | 817% | 231% | 397% | 357% | 180% | 327% | 281% |
| I292G | 324% | 296% | 561% | 210% | 261% | 296% | 165% | 225% | 243% |
| I292H | 357% | 408% | 756% | 200% | 326% | 350% | 158% | 294% | 269% |
| I292K | 372% | 342% | 588% | 211% | 296% | 300% | 168% | 249% | 255% |
| I292L | 365% | 380% | 544% | 210% | 302% | 282% | 158% | 250% | 242% |
| I292M | 245% | 192% | 361% | 180% | 179% | 206% | 157% | 183% | 195% |
| I292N | 332% | 463% | 784% | 188% | 375% | 364% | 147% | 310% | 294% |
| I292Q | 352% | 434% | 706% | 207% | 377% | 345% | 153% | 287% | 272% |
| I292R | 380% | 329% | 653% | 213% | 316% | 325% | 171% | 284% | 257% |
| I292S | 353% | 363% | 640% | 211% | 311% | 326% | 163% | 265% | 270% |
| I292T | 305% | 313% | 495% | 200% | 267% | 294% | 153% | 225% | 244% |
| I292V | 136% | 102% | 144% | 103% | 105% | 106% | 99% | 104% | 106% |
| I292W | 165% | 231% | 194% | 125% | 189% | 123% | 116% | 154% | 110% |
| I292Y | 352% | 481% | 753% | 205% | 358% | 316% | 159% | 268% | 231% |
| I136F/I292F | 143% | 363% | 517% | 104% | 218% | 221% | 89% | 158% | 161% |
| I136R/I292F | 235% | 428% | 591% | 141% | 285% | 242% | 115% | 185% | 178% |
| WT | 100% | 100% | 100% | 100% | 100% | 100% | 100% | 100% | 100% |

TABLE 8

Relative values of activity of enzymes for each BCAA.

| | Relative activity (when activity far Leu is regarded as 100%) | | | | | | | | |
|---|---|---|---|---|---|---|---|---|---|
| | pH 7.0 | | | pH 7.5 | | | pH 8.0 | | |
| | Leu | Ile | Val | Leu | Ile | Val | Leu | Ile | Val |
| I136A | 100% | 57% | 97% | 100% | 70% | 105% | 100% | 95% | 115% |
| I136C | 100% | 57% | 113% | 100% | 75% | 120% | 100% | 107% | 141% |
| I136E | 100% | 55% | 58% | 100% | 65% | 59% | 100% | 72% | 48% |
| I136F | 100% | 86% | 129% | 100% | 102% | 133% | 100% | 111% | 123% |
| I136G | 100% | 52% | 110% | 100% | 75% | 107% | 100% | 102% | 112% |
| I136H | 100% | 59% | 78% | 100% | 87% | 87% | 100% | 98% | 92% |
| I136K | 100% | 76% | 115% | 100% | 88% | 109% | 100% | 95% | 104% |

TABLE 8-continued

Relative values of activity of enzymes for each BCAA.

| | Relative activity (when activity far Leu is regarded as 100%) | | | | | | | | |
|---|---|---|---|---|---|---|---|---|---|
| | pH 7.0 | | | pH 7.5 | | | pH 8.0 | | |
| | Leu | Ile | Val | Leu | Ile | Val | Leu | Ile | Val |
| I136L | 100% | 65% | 104% | 100% | 88% | 116% | 100% | 96% | 112% |
| I136M | 100% | 67% | 113% | 100% | 100% | 144% | 100% | 114% | 142% |
| I136N | 100% | 68% | 78% | 100% | 68% | 74% | 100% | 86% | 72% |
| I136Q | 100% | 107% | 126% | 100% | 81% | 67% | 100% | 95% | 66% |
| I136R | 100% | 77% | 124% | 100% | 105% | 139% | 100% | 115% | 132% |
| I136S | 100% | 80% | 100% | 100% | 76% | 76% | 100% | 92% | 74% |
| I136T | 100% | 85% | 73% | 100% | 69% | 63% | 100% | 78% | 63% |
| I136V | 100% | 72% | 78% | 100% | 68% | 70% | 100% | 72% | 65% |
| I136W | 100% | 69% | 69% | 100% | 74% | 72% | 100% | 86% | 73% |
| I136Y | 100% | 74% | 123% | 100% | 86% | 115% | 100% | 103% | 118% |
| I292A | 100% | 68% | 90% | 100% | 86% | 89% | 100% | 95% | 105% |
| I292C | 100% | 67% | 91% | 100% | 78% | 89% | 100% | 89% | 88% |
| I292D | 100% | 69% | 113% | 100% | 88% | 120% | 100% | 107% | 118% |
| I292E | 100% | 92% | 121% | 100% | 112% | 131% | 100% | 127% | 138% |
| I292F | 100% | 108% | 125% | 100% | 128% | 125% | 100% | 141% | 122% |
| I292G | 100% | 73% | 105% | 100% | 93% | 111% | 100% | 105% | 115% |
| I292H | 100% | 92% | 128% | 100% | 122% | 139% | 100% | 144% | 133% |
| I292K | 100% | 74% | 96% | 100% | 105% | 112% | 100% | 115% | 119% |
| I292L | 100% | 84% | 90% | 100% | 107% | 106% | 100% | 122% | 119% |
| I292M | 100% | 63% | 89% | 100% | 74% | 90% | 100% | 90% | 97% |
| I292N | 100% | 112% | 143% | 100% | 149% | 153% | 100% | 164% | 157% |
| I292Q | 100% | 99% | 122% | 100% | 136% | 132% | 100% | 145% | 139% |
| I292R | 100% | 70% | 104% | 100% | 110% | 120% | 100% | 129% | 118% |
| I292S | 100% | 83% | 110% | 100% | 110% | 122% | 100% | 126% | 130% |
| I292T | 100% | 82% | 98% | 100% | 100% | 116% | 100% | 113% | 124% |
| I292V | 100% | 60% | 64% | 100% | 76% | 81% | 100% | 81% | 84% |
| I292W | 100% | 113% | 71% | 100% | 112% | 77% | 100% | 103% | 74% |
| I292Y | 100% | 110% | 130% | 100% | 131% | 122% | 100% | 131% | 114% |
| I136F/I292F | 100% | 203% | 219% | 100% | 155% | 168% | 100% | 137% | 141% |
| I136R/I292F | 100% | 147% | 153% | 100% | 151% | 136% | 100% | 125% | 122% |
| WT | 100% | 80% | 61% | 100% | 75% | 79% | 100% | 77% | 78% |

Example 7

Evaluation of Thermal Stability

Five solutions of LeuDH WT and the following modified enzymes synthesized in Example 5 were treated with heat at 60, 70 and 80° C. for one hour, and subsequently the activity was measured. A remaining activity of each enzyme solution after the treatment with heat is shown in Table 9. The remaining activity of any modified enzyme after the treatment with heat at 60° C. or 70° C. was higher than that of WT.

TABLE 9

Relative activity after treatment with heat at indicated reaction temperature when activity before treatment is regarded as 100.

| | WT | I292F | I136K | I136F | I136R | I136M |
|---|---|---|---|---|---|---|
| 60° C. | 74 | 92 | 86 | 90 | 91 | 96 |
| 700° C. | 58 | 62 | 67 | 74 | 75 | 74 |
| 80° C. | 0 | 0 | 0 | 0 | 0 | 1 |

INDUSTRIAL APPLICABILITY

The modified enzyme of the present invention is useful for the rapid measurement of the total branched-chain amino acid concentration. The modified enzyme of the present invention is also useful for the measurement of any branched-chain amino acid and/or the production of derivatives of any branched-chain amino acid. The modified enzyme of the present invention is further useful as a liquid reagent. The analysis method of the present invention is useful for the diagnosis of diseases such as cirrhosis or hepatic encephalopathy.

While the invention has been described in detail with reference to preferred embodiments thereof, it will be apparent to one skilled in the art that various changes can be made, and equivalents employed, without departing from the scope of the invention. Each of the aforementioned documents is incorporated by reference herein in its entirety.

---

The invention claimed is:

1. A modified leucine dehydrogenase enzyme comprising at least one amino acid mutation as compared to a non-modified leucine dehydrogenase enzyme, wherein said modified leucine dehydrogenase is improved in one or more properties selected from the group consisting of:

(a) substrate specificities for L-leucine, L-isoleucine, and L-valine;

(b) activity for any branched-chain amino acid;

(c) thermal stability, and (d) combinations thereof, wherein said modified leucine dehydrogenase is:

(A) a protein comprising the amino acid sequence of SEQ ID NO: 2; but having a substitution of isoleucine in the TGI motif with an amino acid selected from the group consisting of methionine, arginine, histidine, phenylalanine, leucine, lysine, cysteine, tyrosine, alanine, glycine, serine, asparagine, and tryptophan, (B) a protein comprising the amino acid sequence of SEQ ID NO: 2; but having a substitution of isoleucine in the GVI motif with an amino acid selected from the group consisting of phenylalanine, histidine, asparagine, tyrosine, leucine, lysine, glutamine, arginine, aspartic acid, threonine, glutamic acid, serine, cysteine, alanine, glycine, valine, tryptophan, and methionine, (C) a protein comprising the amino acid sequence of SEQ ID NO: 2; but having a substitution of isoleucine in the TGI motif with an amino acid selected from the group consisting of methionine, arginine, histidine, phenylalanine, leucine, lysine, cysteine, tyrosine, alanine, glycine, serine, asparagine, and tryptophan; and a substitution of isoleucine in the GVI motif with an amino acid selected from the group consisting of phenylalanine, histidine, asparagine, tyrosine, leucine, lysine, glutamine, arginine, aspartic acid, threonine, glutamic acid, serine, cysteine, alanine, glycine, valine, tryptophan, and methionine, and (D) a protein as described in (A), (B), or (C) above, but also having one to ten additional mutations of amino acid residues.

2. The modified leucine dehydrogenase enzyme according to claim 1, wherein said amino acid sequence is SEQ ID NO: 2.

3. A method of analyzing branched-chain amino acids, comprising measuring all branched-chain amino acids contained in a test sample using the modified leucine dehydrogenase enzyme according to claim 1.

4. The method according to claim 3, comprising mixing the test sample with nicotinamide adenine dinucleotide ($NAD^+$) and detecting NADH formed from $NAD^+$ by an action of the modified leucine dehydrogenase enzyme.

5. A kit for analyzing branched-chain amino acids, comprising the modified enzyme according to claim 1.

6. The kit for analyzing branched-chain amino acids according to claim 5, further comprising at least one of a buffer solution or a buffer salt for a reaction and nicotinamide adenine dinucleotide ($NAD^+$).

* * * * *